(12) United States Patent
Lee

(10) Patent No.: US 10,501,854 B2
(45) Date of Patent: Dec. 10, 2019

(54) LOCALIZED EXCESS PROTONS AND METHODS OF MAKING AND USING SAME

(71) Applicant: James Weifu Lee, Chesapeake, VA (US)

(72) Inventor: James Weifu Lee, Chesapeake, VA (US)

( * ) Notice: Subject to any disclaimer, the term of this patent is extended or adjusted under 35 U.S.C. 154(b) by 464 days.

(21) Appl. No.: 15/202,214

(22) Filed: Jul. 5, 2016

(65) Prior Publication Data

US 2017/0009357 A1  Jan. 12, 2017

Related U.S. Application Data

(60) Provisional application No. 62/231,402, filed on Jul. 6, 2015.

(51) Int. Cl.

| | |
|---|---|
| C02F 1/46 | (2006.01) |
| C25B 1/06 | (2006.01) |
| C25B 1/10 | (2006.01) |
| C23F 1/14 | (2006.01) |
| C12P 19/32 | (2006.01) |

(52) U.S. Cl.
CPC .......... *C25B 1/06* (2013.01); *C12P 19/32* (2013.01); *C12Y 306/03014* (2013.01); *C23F 1/14* (2013.01); *C25B 1/10* (2013.01); *Y02E 60/366* (2013.01); *Y02P 20/129* (2015.11)

(58) Field of Classification Search
CPC . C25B 1/06; C25B 1/10; Y02P 20/129; C02F 1/46; C02F 1/469
See application file for complete search history.

(56) References Cited

U.S. PATENT DOCUMENTS

| | | |
|---|---|---|
| 4,759,817 A | 7/1988 | Aigo |
| 4,859,281 A | 8/1989 | Goltz |

(Continued)

FOREIGN PATENT DOCUMENTS

GB    319656 A    5/1930

OTHER PUBLICATIONS

Lim, J.K. et al., "Energy Conservation by Oxidation of Formate to Carbon Dioxide and Hydrogen via a Sodium Ion Current in Hyperthermophilic Archaeon", PNAS, vol. 111, No. 31, pp. 11497-11502, Aug. 5, 2014.

(Continued)

*Primary Examiner* — Arun S Phasge

(57) ABSTRACT

Localized excess protons are created with an open-circuit water electrolysis process using a pair of anode and cathode electrodes for a special excess proton production and proton-utilization system to treat a substrate material plate/film by forming and using an excess protons-substrate-hydroxyl anions capacitor-like system. The technology enables protonation and/or proton-driven oxidation of plate/film and/or membrane materials in a pure water environment. The present invention represents a remarkable clean "green chemistry" technology that does not require the use of any conventional acid chemicals including nitric and sulfuric acids for the said industrial applications. The application of localized excess protons provides a special energy recycling and renewing technology function to extract latent heat including molecular thermal motion energy at ambient temperature for generating local proton motive force (equivalent to Gibbs free energy) to do useful work such as driving ATP synthesis and proton-driven oxidation of certain substrate metal atoms.

20 Claims, 15 Drawing Sheets

(56) References Cited

U.S. PATENT DOCUMENTS

| | | |
|---|---|---|
| 2002/0177107 A1 | 11/2002 | Moran |
| 2011/0143549 A1 | 6/2011 | Tange et al. |
| 2012/0138468 A1 | 6/2012 | Sivan et al. |
| 2014/0014522 A1 | 1/2014 | Mayer et al. |
| 2014/0179107 A1 | 6/2014 | Nowling |

OTHER PUBLICATIONS

Lee, J.W., "Proton-Electrostatic Localization: Explaining the Bioenergetic Conundrum in Alkalophilic Bacteria", Bioenergetics, vol. 4, Issue 1, pp. (2015).

Lee, J.W. et al., "Characterization of Biochars Produced from Cornstovers for Soil Amendment", Envrion, Sci. Technol. 44 pp. 7970-7974 (2010).

Heimburg, T., "The Capacitance and Electromechanical Coupling of Lipid Membranes Close to Transitions: The Effect of Electrostriction", Biophysical Journal, vol. 103, pp. 918-929, Sep. 2012.

Gramse, G., "Nanoscale Measurement of the Dielectric Constant of Supported Lipid Bilayers in Aqueous Solutions with Electrostatic force Microscopy", Biophysical Journal, vol. 104, pp. 1257-1262, Mar. 2013.

Dudkina, N.V., "Structure and Function of Mitochondrial Supercomplexes", Biochimica et Biophysica Acta 1797, pp. 664-670 (2010).

Saeed and Lee, "Experimental Demonstration of Localized Excess Protons at a Water-Membrane Interface", Bioenergetics 4.2 (2015).

Vinkler, C. et al., "Initial Formation of ATP in Photophosphorylation Does Not Require a Proton Gradient", FEBS Letters, vol. 96, No. 1, pp. 129-134, Dec. 1978.

International Search Report and Written Opinion of the International Searching Authority, International Application No. PCT/US16/40978, dated Oct. 7, 2016.

Lee, "Proton-Electrostatics Hypothesis for Localized Proton Coupling Bioenergetics", Bioenergetics 2012.

International Preliminary Report on Patentability, International Patent Application No. PCT/US2016/040978.

McLaughlin, S., "The Electrostatic Properties of Membranes", Annu. Rev. Biophys. Biophys. Chem 18:113-136 (1989).

Nicholls and Ferguson, Bioenergetics, Chapter 3, Quantitative Bioenergetics: The Measurement of Driving Forces, Elsevier Ltd., pp. 27-51 (2013).

Skjemstad et al., "Measurement of Cation Exchange Capacity of Organic-Matter Fractions from Soils using a Modified Compulsive Exchange Method", Communications in Soil Science and Plant Analysis, 39:926-937 (2008).

Skulachev et al., Principles of Bioenergetics, ISBN 978-3-642-33429-0, Springer-Verlag (2013).

McMillan et al., "A1A0-ATP Synthase of Methanobrevibacter ruminantium Couples Sodium Ions for ATP Synthesis under Physiological Conditions", The Journal of Biological Chemistry, vol. 286, No. 46, pp. 39882-39892, Nov. 18, 2011.

Marcel Pourbaix, "Applications of Electrochemistry in Corrosion Science and in Practice", Corrosion Science, vol. 14, pp. 25-82 (1974).

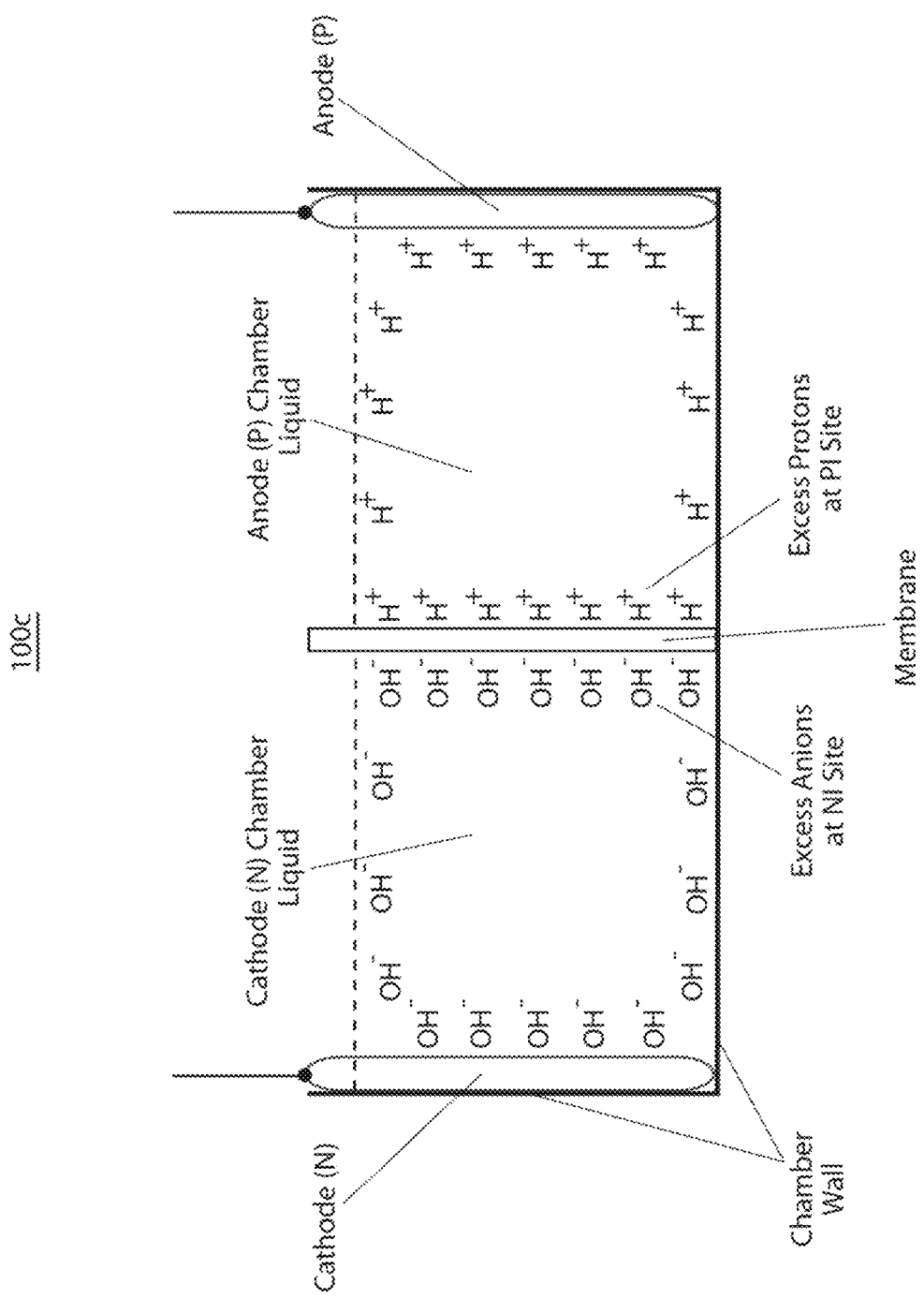

LOCALIZED EXCESS PROTONS AND METHODS OF MAKING AND USING SAME

CROSS-REFERENCE TO RELATED APPLICATIONS

This application claims priority and benefit from U.S. Provisional Application No. 62/231,402 filed on Jul. 6, 2015, which is incorporated herein by reference in its entirety.

FIELD OF THE INVENTION

The present invention is directed to methods and systems for creating electrostatically localized excess protons to be utilized as a clean "green chemistry" technology for industrial applications such as acid-etching and/or protonation of certain micro/nanometer materials without the use of conventional acid chemicals such as nitric and sulfuric acids and as a special energy-renewing technology process to utilize latent heat for generation of local proton motive force (equivalent to Gibbs free energy) to do work such as driving ATP synthesis.

BACKGROUND

The newly developed proton-electrostatics localization hypothesis in understanding proton-coupling bioenergetics over the Nobel-prize work of Peter Mitchell's chemiosmotic theory (Lee 2012 Bioenergetics 1:104; doi:10.4172/2167-7662.1000104) resulted in the following new proton motive force (pmf) equation that may potentially represent a major breakthrough advance in the science of bioenergetics:

$$pmf(\Delta p) = \Delta \psi + \frac{2.3RT}{F}\left(pH_{nB} + \log_{10}\left(\frac{C}{S} \cdot \frac{\Delta \psi}{l \cdot F\left(\prod_{i=1}^{n}\left\{K_{Pi}\left(\frac{[M_{pB}^{i+}]}{[H_{pB}^{+}]}\right) + 1\right\}\right)} + [H_{pB}^{+}]\right)\right) \quad [1]$$

Where $\Delta \psi$ is the electrical potential difference across the membrane; $pH_{nB}$ is pH of the cytoplasmic bulk phase; $[H^{+}_{pB}]$ is the proton concentration in the periplasmic bulk aqueous phase; C/S is the specific membrane capacitance; l is the thickness for localized proton layer; $K_{Pi}$ is the equilibrium constant for non-proton cations ($M^{i+}_{pB}$) to exchange for localized protons; and $[M^{i+}_{pB}]$ is the concentration of non-proton cations in liquid culture medium (Lee 2015 Bioenergetics 4: 121. doi:10.4172/2167-7662.1000121).

The core concept of the proton-electrostatics localization hypothesis is based on the premise that a biologically-relevant water body, such as the water within a bacterium, can act as a proton conductor in a manner similar to an electric conductor with respect to electrostatics. This is consistent with the well-established knowledge that protons can quickly transfer among water molecules by the "hops and turns" mechanism. From the charge translocation point of view, it is noticed that hydroxyl anions are transferred in the opposite direction of proton conduction. This understanding suggests that excess free protons in a biologically-relevant water body behave like electrons in a perfect conductor. It is well known for a charged electrical conductor at static equilibrium that all extra electrons reside on the conducting body's surface. This is expected because electrons repel each other, and, being free to move, they will spread out to the surface. By the same token, it is reasonable to expect that free excess protons (or conversely the excess hydroxyl anions) in a biologically-relevant water body will move to its surface. Adapting this view to excess free hydroxyl anions in the cytoplasm (created by pumping protons across the cytoplasm membrane through the proton-transfer-coupled respiratory electron transport into the liquid medium outside the cell), they will be electrostatically localized along the water-membrane interface at the cytoplasmic (n) side of the cell membrane. In addition, their negative charges (OH$^-$) will attract the positively charged species (H$^+$) outside the cell to the membrane-water interface at the periplasmic (p) side.

That is, when excess hydroxyl anions are created in the cytoplasm by the oxidative-driven proton pump across the membrane leaving excess protons outside the cell, the excess hydroxyl anions in the cytoplasm will not stay in the bulk water phase because of their mutual repulsion. Consequently, they go to the water-membrane interface at the cytoplasmic side of the membrane where they then attract the excess protons at the periplasmic side of the membrane, forming an "excess anions-membrane-excess protons" capacitor-like system. Therefore, the proton capacitor concept is used to calculate the effective concentration of the localized protons $[H_L^+]^0$ at the membrane-water interface in a pure water-membrane-water system assuming a reasonable thickness (l) for the localized proton layer using the following equation:

$$[H_L^+]^0 = \frac{C}{S} \cdot \frac{\Delta \psi}{l \cdot F} = \frac{\Delta \psi \cdot \kappa \cdot \varepsilon_0}{d \cdot l \cdot F} \quad [2]$$

where C/S is the membrane capacitance per unit surface area; F is the Faraday constant; $\kappa$ is the dielectric constant of the membrane; $\varepsilon_o$ is the electric permittivity; d is the thickness of the membrane; and l is the thickness of the localized proton layer. This proton-capacitor equation [2] is a foundation for the newly revised pmf equation [1], which includes an additional term that accounts for the effect of non-proton cations exchanging with the localized protons.

Recently, using nanoscale measurements with electrostatic force microscopy, the dielectric constant ($\kappa$) of a lipid bilayer was determined to be about 3 units, which is in the expected range of 2~4 units (Grames et al, Biophysical Journal 104: 1257-1262; Heimburg 2012 Biophysical Journal 103: 918-929.). Table 1 lists the calculation results for localized protons for a theoretical pure water-membrane-water system with Eq. 2 using a lipid membrane dielectric constant $\kappa$ of 3 units, membrane thickness d of 4 nm, trans-membrane potential difference $\Delta \psi$ of 180 mV, and three assumed values for the proton layer thickness of 0.5, 1.0, and 1.5 nm.

TABLE 1

Calculation of localized protons with Equation 2 in a theoretical pure water-membrane-water system using a membrane dielectric constant $\kappa$ of 3, membrane thickness d of 4 nm, and trans-membrane potential difference $\Delta \psi$ of 180 mV.

| Assumed thickness (l) of localized proton layer | 0.5 nm | 1.0 nm | 1.5 nm |
|---|---|---|---|
| Localized proton density per unit area (moles H$^+$/m$^2$) | 1.238 × 10$^{-8}$ | 1.238 × 10$^{-8}$ | 1.238 × 10$^{-8}$ |

TABLE 1-continued

Calculation of localized protons with Equation 2 in a theoretical pure water-membrane-water system using a membrane dielectric constant κ of 3, membrane thickness d of 4 nm, and trans-membrane potential difference Δψ of 180 mV.

| | | | |
|---|---|---|---|
| Effective concentration of localized proton ($[H_L^+]^0$) | 24.76 mM | 12.38 mM | 8.25 mM |
| Effective pH of localized proton layer ($pH_L^0$) | 1.61 | 1.91 | 2.08 |

As shown in Table 1, the localized proton density per unit area was calculated to be $1.238 \times 10^{-8}$ moles $H^+/m^2$. The calculated effective concentration of localized proton ($[H_L^+]^0$) was in a range from 8.25 mM to 24.76 mM if the localized proton layer is around 1.0±0.5 nm thick. The calculated effective pH of localized proton layer ($pH_L^0$) was 1.61, 1.91, and 2.08 assuming that the localized proton layer is 0.5, 1.0, and 1.5-nm thick, respectively. This calculation result also indicated that localized excess protons may be created at a water-membrane interface for possible industrial applications such as acid-etching of certain metals and/or protonation of certain micro/nanometer materials without requiring the use of conventional acid chemicals such as nitric and sulfuric acids.

SUMMARY OF THE INVENTION

The present invention discloses a series of innovative methods for creating electrostatically localized excess protons to be utilized as a clean "green chemistry" technology for industrial applications such as acid-etching and/or protonation of certain micro/nanometer materials without requiring the use of conventional acid chemicals such as nitric and sulfuric acids. A special energy-recycling and renewing technology is provided with the associated methods to extract latent heat energy including molecular thermal motion energy for generating local proton motive force (equivalent to Gibbs free energy) to do useful work such as driving ATP synthesis.

The present invention discloses a series of innovative methods that creates localized excess protons at a water-substrate or water-membrane interface for industrial process applications. According to one of the various embodiments, an open-circuit water electrolysis process uses a pair of anode and cathode electrodes in a special excess proton production and proton-utilization system, which can treat a series of substrate plate/film materials by forming and using an excess protons-substrate-hydroxyl anions capacitor-like system. The technology enables protonation and/or proton-driven oxidation of plate/film materials in a pure water environment. The present invention represents a remarkable clean "green chemistry" technology that does not require the use of any conventional acid chemicals including nitric and sulfuric acids for the said industrial applications and, more importantly, as a special tool to utilize latent heat energy from the environment for generation of local proton motive force (equivalent to Gibbs free energy) to do useful work such as driving ATP synthesis.

Creating and using excess protons-substrate-hydroxyl anions capacitor-like systems has been demonstrated through an experimental study in the Lee Laboratory at Old Dominion University. According to this experimental study, excess protons do not stay in a bulk water liquid phase in the anode chamber. Instead, they electrostatically localize at the water-membrane interface at the anode chamber and attract the excess hydroxyl anions of the cathode chamber water to the other side of the substrate film. The effective concentration of localized protons at the water-membrane interface can be well above 0.1 mM, making them potent enough to enable protonation of synthetic substrate materials such as (poly)aniline. The use of localized excess protons as a micro/nanometer tool can also perform proton-etching of certain substrate materials such as aluminum, iron, and copper to create various desirable proton-etching patterns on a substrate membrane, film, or a substrate plate.

Since the excess-proton treatment such as the protonation of synthetic substrate materials such as (poly)aniline or proton-etching of micro/nanometer materials can be operated in a pure water environment with a neutral bulk-phase pH, when the so-treated substrate is taken out of the pure water chamber system, it could immediately emerge as a clean quality product (any residual pure water can be readily dried off) without requiring any additional washing/cleaning step that a conventional acid-treatment process would require. Therefore, the method disclosed in this invention represents a remarkably clean "green chemistry" technology.

The application of localized excess protons with a liquid membrane chamber system provides a special energy-recycling and renewing technology process function to extract latent heat from ambient temperature environment including the molecular thermal motion energy for generating local proton motive force (equivalent to Gibbs free energy) to do useful work such as driving ATP synthesis.

According to one of the various embodiments, the liquid membrane chamber system is a multi-chamber excess proton production and utilization system comprising: a) Multiple membranes are placed in between an anode chamber and a cathode chamber, forming multiple induction chambers among multiple membranes; b) Chamber wall is made of water impermeable, chemically-inert and electrically insulating materials; c) Proton users comprising ATP synthase are embedded with each of the multiple membranes.

According to another of the various embodiments, the special energy-recycling and renewing technology process has a special feature that employs multiple membranes, each with a relatively smaller membrane potential, in a multi-chamber system that can be employed with use of a relatively small electrolysis voltage for generating excess protons to extract latent heat molecular thermal motion energy to create a total pmf value much larger than the input electrolysis voltage.

According to another of the various embodiments in accordance of the present invention, the special energy-recycling and renewing technology process to extract latent heat energy associated with localized protons for generating local proton motive force (equivalent to Gibbs free energy) comprising the following steps and features: a) Through use of the "open-circuit" water-electrolysis process, excess protons are generated in anode liquid chamber while excess hydroxyl anions are created in cathode liquid chamber; b) The generated excess protons electrostatically localize themselves primarily along the water-membrane interface at the positive (anodic) interface (PI) site while the excess anions electrostatically localize themselves primarily along the water-membrane interface at the negative (cathodic) interface (NI) site; c) The excess protons at PI site in conjunction with the excess anions at NI site electrostatically induce the formation of induced anions at the induced negative interface (INI) site(s) and the induced protons at the induced positive interface (IPI) site(s) in the induction liquid chambers; d) The formation of the electrostatically localized protons at the water-membrane interface constitutes a type of "negative entropy" event resulting in the formation of multiple "localized protons-membrane-anions" capacitor-like structures; e) The formation of multiple "localized protons-membrane-anions" capacitor-like structures results in the formation of membrane potential across each of the membranes; f) In addition to the generation of membrane potential, significant amount of "bonus" local proton motive force is also created from the "entropy effect" of the localized protons since their thermal molecular motion energy can drive nanometer scale molecular machines such as $F_0F_1$-ATP synthase embedded in the membrane.

According to another of the various embodiment, the special energy-recycling and renewing technology process has a preferred practice to place the proton-generating anode electrode well into the bulk phase liquid and to keep the mouths of proton users being located rightly within the localized excess protons layer along the membrane surface, for the best effect to utilize the latent heat associated with the molecular thermal motion energy of localized protons to perform useful work such as driving the synthesis of ATP, enhancing the protonation of certain synthetic polymer materials, and driving the proton-etching of certain substrate metal plates.

According to exemplary embodiments, the utilization of latent heat with localized protons to recycle/utilize the fully dissipated waste heat energy, which conventionally is thought to be totally unusable, generates local pmf to do useful work. This provides an innovative method to renew the totally "dead" latent heat energy in ambient temperature environment that according to the Second Law of Thermodynamics would be completely unusable. That is, the "dead" latent heat energy can now be reborn to create new Gibbs free energy in the form of local pmf in accordance with the present invention. Therefore, it fundamentally represents a special energy-recycle and energy-renew-related technology.

BRIEF DESCRIPTION OF THE DRAWINGS

FIG. 1c presents an embodiment showing the likely distribution of excess protons and excess hydroxyl anions in the two water chambers separated by a membrane when electrolysis voltage is turned off.

DETAILED DESCRIPTION

Exemplary embodiments in accordance with the present invention are directed to a series of systems and methods based on the creation of excess protons and their industrial process applications. Accordingly, the present invention provides, inter alia, methods for creating localized excess protons that can be utilized for clean "green chemistry" technologies in industrial applications such as metal acid washing (etching) and/or protonation of certain micro/nanometer materials without requiring the usage of conventional acid chemicals such as nitric and sulfuric acids. A special energy technology is provided with the associated methods to extract latent heat energy including molecular thermal motion energy for generating local proton motive force (equivalent to Gibbs free energy) to do useful work, which may have seminal scientific and practical implications for energy and environmental sustainability on Earth. The various aspects of the present invention are described in further detail hereinbelow.

Figure 1A:
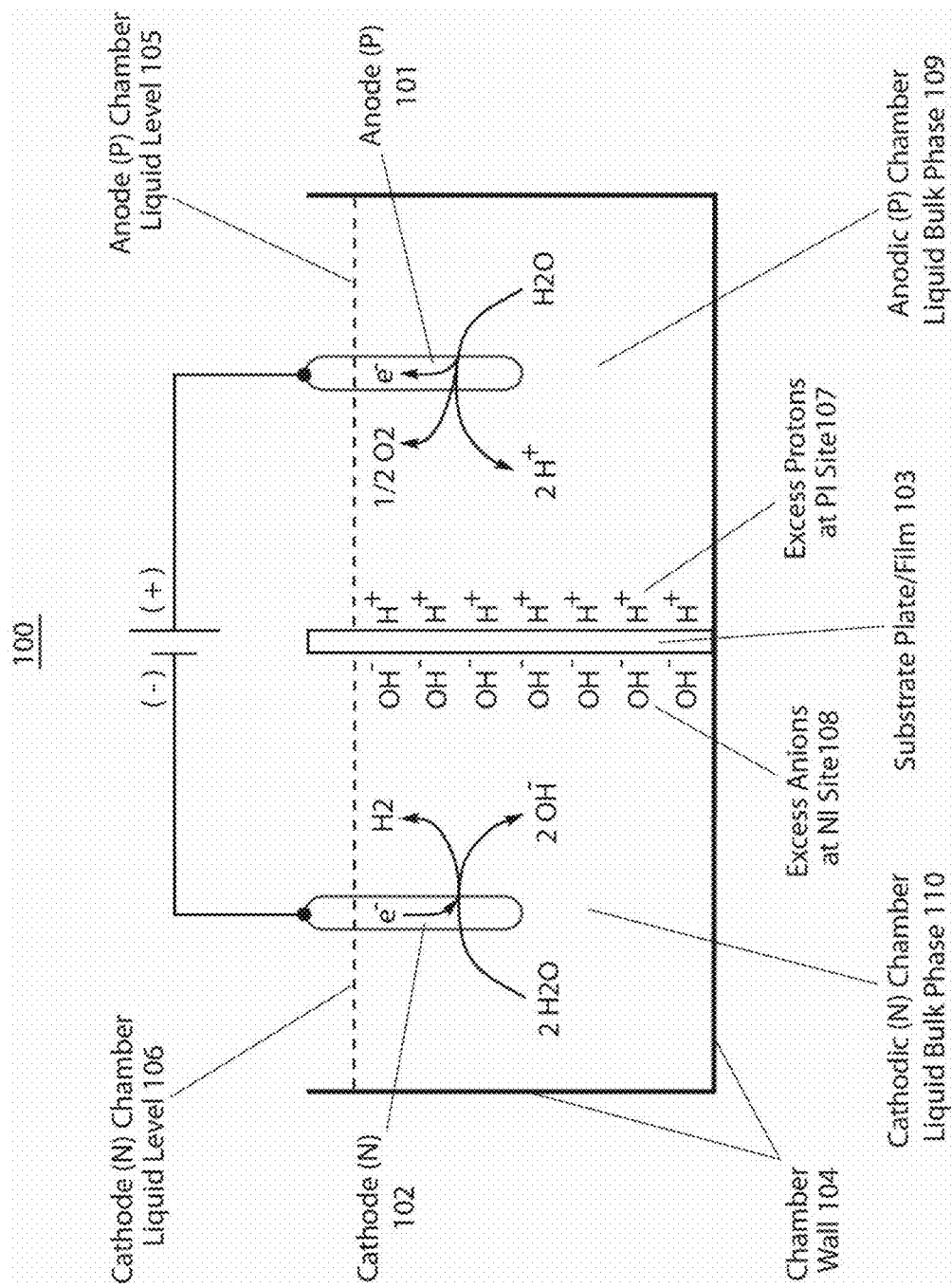
FIG. 1a presents an embodiment that produces excess protons and hydroxyl anions through an "open-circuit" water electrolysis process and results in an "excess protons-substrate-hydroxyl anions" capacitor-like system for industrial applications.

Referring to FIG. 1a, in one embodiment, an excess proton production system 100 is illustrated. The excess proton production system includes a substrate plate/film 103 that is placed in between an anode chamber and a cathode chamber. The chamber wall 104 is made of water impermeable and chemically-inert materials such as Teflon, plastic material, and glass, which are unreactive even if under high power voltage. The substrate plate/film (membrane) 103 joins with the chamber wall 104 using a water-tight seal, resulting in the two separate chambers: the anode water chamber and the cathode water chamber.

According to one of the various embodiments, both the anode and cathode chambers are filled with pure water. The anode (N) chamber liquid level 105 is set preferably at the same level as the cathode (N) chamber liquid level 106. Both the anode (P) 101 and cathode (N) 102 are typically made of stable electrode materials such as metallic platinum, palladium, gold, copper, certain stainless steels, graphite, micro/nanometer carbon fiber materials and any combinations thereof. The anode and cathode are placed into the anodic (P) liquid bulk phase 109 and the cathodic (N) liquid bulk phase 110, respectively. The excess protons and excess hydroxyl anions are generated through the use of "open-circuit" water-electrolysis by applying a direct current (DC) voltage across the anode (P) 101 and cathode (N) 102 electrodes (FIG. 1a) in the two water bodies separated by the substrate plate/film 103. In accordance of the present invention, the excess protons produced by the "open-circuit" water-electrolysis process localize at the water-substrate interface (PI Site 107) along the surface of the plate/film (or membrane) where they attract the excess hydroxyl anions at the other side (NI Site 108) of the substrate plate, forming an "excess protons-plate-excess anions" capacitor-like structure.

According to one of the various embodiments, the direct current (DC) electric voltage applied across the anode and cathode electrodes is selected from the group consisting of 1.23 V, 1.5 V, 2 V, 3 V, 4 V, 5 V, 6 V, 7 V, 8 V, 10 V, 11 V, 12 V, 13 V, 14 V, 15 V, 17 V, 18 V, 19 V, 20 V, 21 V, 22 V, 23 V, 24 V, 25 V, 26 V, 27 V, 28 V, 29 V, 30 V, 31 V, 32 V, 35 V, 36 V, 40 V, 50 V, 60 V, 70 V, 80 V, 90 V, 100 V, 150 V, 200 V, 250V, 300 V, 400 V, 500 V, 600 V, 700 V, 800 V, 900 V, 1000V, 1200 V, 1500 V, 2000 V, 2500 V, 3000 V, 4000V, 5000 V, 6000 V, 8000 V, 10,000 V, 12,000 V, 15,000 V, 20,000 V, 25,000V, 30,000 V and/or within a range bounded by any two of these values. When necessary to work with a voltage above 36 V, certain electric safety protocol must be strictly followed to prevent any electric shocks and accidents.

The effective concentration of the localized excess protons at the water-substrate interface can be at a value selected from the group consisting of 0.1 mM, 1 mM, 2 mM, 3 mM, 5 mM, 10 mM, 20 mM, 30 mM, 40 mM, 50 mM, 60 mM, 70 mM, 80 mM, 90 mM 100 mM, 120 mM, 150 mM, 200 mM, 300 mM, 500 mM, 1 M, 2 M, 3 M, 5M, 10 M and/or within a range bounded by any two of these values, which are often orders of magnitude higher than that indicated by the bulk water liquid phase pH measurements. Therefore, according to one of the various embodiments, this type of localized excess protons may be utilized to protonate certain special materials such as (poly)aniline and/or to treat certain synthetic materials and metal surfaces such as aluminum, iron and copper by "acid etching" or oxidation by protons.

According to one of the various embodiments, the substrate plate/film (or membrane) is selected from the group consisting of protonatable materials such as (poly)aniline, and certain metal surfaces such as aluminum, iron, copper, and any combination thereof.

According to one of the various embodiments, the protonatable materials such as (poly)aniline can be protonated at the PI site 107 (FIG. 1a) as shown in the following protonation reaction:

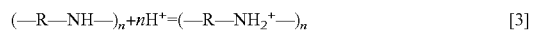

$$(-R-NH-)_n + nH^+ = (-R-NH_2^+-)_n \qquad [3]$$

Whereas certain polymer substrate such as a protonated (poly)aniline film may be deprotonated at the NI site 108 (FIG. 1a) according to the following de-protonation process reaction:

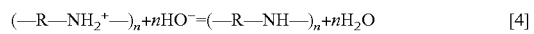

$$(-R-NH_2^+-)_n + nHO^- = (-R-NH-)_n + nH_2O \qquad [4]$$

Therefore, use of this invention can create a special polymer film with an asymmetric proton distribution across the film that may confer certain special functions such as diodic properties.

According to one of the various embodiments, certain metal surfaces such as aluminum, iron, and copper can be etched or oxidized by the excess protons at the PI site 107 (FIG. 1a) through the following proton-etching process reaction:

$$Al + 2H^+ = Al^{++} + H_2 \qquad [5]$$

This proton-etching process differs from the conventional metal electroetching process that involves the use of a solution of an electrolyte (salt) rather than pure water. In the conventional metal electroetching process, the metal piece to be etched is connected to the positive pole of a source of direct electric current. A piece of the same metal is connected to the negative pole of the direct current source and is called the cathode. In order to reduce unwanted electrochemical effects, the anode and the cathode should be of the same metal. Similarly, the cation of the electrolyte should be of the same metal as well. When the current source is turned on, the metal of the anode is dissolved and converted into the same cation as in the electrolyte and at the same time an equal amount of the cation in the solution is converted into metal and deposited on the cathode.

In contrast, the proton-etching process does not require any electrolyte (salt) since it uses pure water. Furthermore, the metal piece (substrate 103) to be etched is not directly connected with the anode. Consequently, the metal of the anode 101 is not dissolved and there is no metal deposition at the cathode 102.

According to one of the various embodiments, this proton-etching process may be employed as a micro/nanometer fabrication tool with an acid-resistant material "resist" as mask coating material just like PMMA does in the current e-beam lithographic technique. Here, the etching action will be exerted by a layer of excess protons localized at the water-substrate interface according to the proton electrostatic localization theory. With the use of proton "resist" masks, only part of the substrate surface that is not protected by a proton "resist" mask will be etched. In this way, many proton-etching patterns such as the word "ODU" and/or any other patterns like a round disk pattern (FIG. $6P_t$) may be created on a substrate. One of the advantages is that this method uses just water with DC electrodes operated with nearly an open-circuit water electrolysis process (with minimal electricity energy consumption), and no additional chemicals such as salts, nitric acid or chloric acid are needed here.

Since the treatment (such as the protonation of synthetic substrate materials such as (poly)aniline or proton-etching of micro/nanometer materials) can be operated in a pure water environment with neutral bulk pH, when the so-treated substrate is taken out of the chamber, it may immediately emerge as a quality product with the cleanness of pure water without requiring any additional washing/cleaning step that a conventional acid-treatment process would require. Thus, the method disclosed in this invention represents a remarkably clean "green chemistry" technology.

Figure 1B:
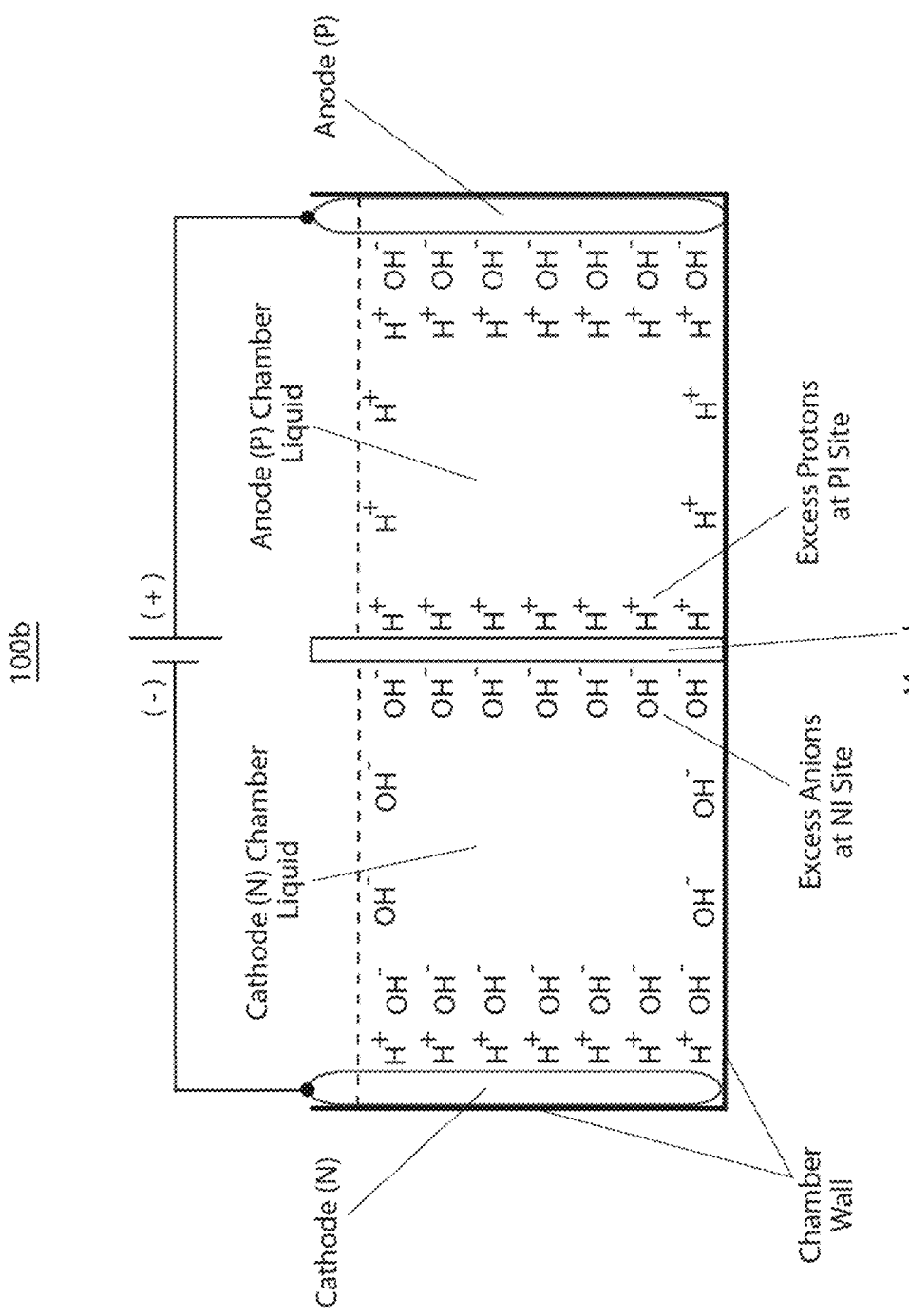
FIG. 1b presents an embodiment showing that the excess proton monolayer at the water-membrane interface is extended from a secondary proton layer of the "electric double layer" that covers the anode surface when electrolysis voltage is applied.

In addition, as illustrated in FIG. 1b, the present invention in one of the various embodiments has created and demonstrated the formation of a localized excess protons layer at the water-membrane interface in an anode water-membrane-water cathode system, where excess protons were generated by water electrolysis in an anode electrode chamber while excess hydroxyl anions were created in a cathode chamber. When a positive voltage is applied to the anode electrode in water, it first attracts the hydroxyl anions to anode electrode surface and then some of counter ions (protons) distribute themselves near the anions layer, forming a typical "electric double layer" on the anode surface (FIG. 1b, right side). When a significant number of excess protons are produced by water electrolysis (in mimicking a biological proton production process such as the respiratory proton pumping system and the photosynthetic water-splitting process) in the anode chamber, the excess protons electrostatically distribute themselves at the water-surface (including the membrane surface) interface around the water body (including a part of the "electric double layer" at the anode surface). From here, it can be seen that the excess proton layer formed at the water-membrane is apparently a type of special extension from the secondary (proton) layer of the "electric double layer" at the anode. The excess proton layer at the water-membrane interface electrostatically attracts the excess hydroxyl anions in the cathode chamber at the other side of the member, forming an excess anions-membrane-excess proton capacitor-like structure.

Since the membrane is an insulator layer (not an electrode), the excess proton layer at the water-membrane interface is likely to be a special monolayer (with a thickness probably of about 1 nm), but definitely not an "electric double layer". This novel feature of being an excess proton monolayer at the membrane-interface is also consistent with the fundamental understanding of the "electric double layer" theory since the excess proton layer created and demonstrated here can be understood as a kind of special extension from the second (proton) layer of the anode's "electric double layer" (FIG. 1b, right side) around the proton-conductive water body.

When the electrolysis voltage is turned off, the electrical polarization at both anode and cathode disappears and so does the "electric double layer", leaving only the excess proton layer around the anode chamber water body and the similarly formed excess hydroxyl (anions) layer around the cathode chamber water body as illustrated in FIG. 1c. The excess anions-membrane-excess proton capacitor (shown in the middle of FIG. 1c) may represent a proof-of-principle mimic for an energized biological membrane such as a mitochondrial membrane system at its energized resting state.

The excess protons created and demonstrated experimentally here have special features. Unlike a charge-balanced (1,1) electrolyte, excess protons do not have counter ions since their counter ions, the excess anions, are on the other side of the membrane as shown in FIG. 1c. Therefore, the common "electric double layer" models (McLaughlin, 1989 Annual Review of Biophysics and Biophysical Chemistry, 18:113-136) including the Gouy-Chapman theory and Debye shielding length concept may not necessarily be used as an accurate description for the excess proton layer that has now been experimentally demonstrated here in accordance with one of the various embodiments of the present invention.

The Debye shielding length concept is commonly used to estimate the thickness of an electric double layer. It however may not be able to accurately estimate the thickness of this special excess proton monolayer demonstrated in accordance of the present invention. Since both the "electric double layer" models (including the Gouy-Chapman theory) and the Debye shielding length concept are based on charge-balanced electrolytes with cations and anions being together in the same water body, they may not be applicable to the special excess protons that do not have counter ions in their associated water body since their counter ions (excess hydroxyl anions) are completely in a separated water body on the other side of the membrane as illustrated in FIG. 1c.

Furthermore, the excess protons created and demonstrated experimentally here are fundamentally different from the protons that are attracted to the biological membrane surface by the membrane's fixed surface charges such as the negatively-charged phosphate groups of a typical biological membrane that may attract protons and other cations to its surface forming an electric double layer along the membrane negatively charged surface as expected by the Gouy-Chapman theory. That type of membrane surface charge-associated electric double layer (associated with the "surface potentials") always exists even when the proton motive force (pmf) is completely zero. Therefore, the membrane surface potentials-attracted protons do not contribute to the proton motive force that drives the flow of protons across the membrane for ATP synthesis as pointed out also in bioenergetics textbooks (Nicholls & Ferguson 2013 Bioenergetics, 27-51, Academic Press). In contrast, the excess protons can electrostatically localize themselves to the water-membrane interface without requiring any membrane surface charges, which are fundamentally different from those charge-balanced protons attracted by the membrane surface potentials. The concept of excess protons, however, is not to be confused with the commonly known charge-balanced protons in water and biological systems.

The creation of an excess protons layer has recently been experimentally demonstrated at a water-membrane interface in an anode water-membrane-water cathode system using a charge-neutral and inert membrane such as a Teflon membrane in mimicking the biological systems (Saeed and Lee 2015 Bioenergetics 4: 127. doi:10.4172/2167-7662.1000127). In fact, it is this type of free excess protons that have the dynamic properties to be coupled to ATP synthase that are relevant to the proton motive force in biological systems.

Therefore, the excess protons layer demonstrated through the experiments represent an advance having scientific and technological implications. For example, the excess protons layer may be employed as a special tool to enable the extraction of latent heat molecular thermal motion energy to create additional protonic motive force (equivalent to Gibbs free energy) to do useful work as described herein.

According to one of the preferred embodiments, liquid water is used that does not contain too much dissolved gases for the creation of excess protons layer at a membrane-water interface. For example, during the winter season when the laboratory temperature (typically about 22° C.) is significantly higher than the outside water supplying sources, the Millipore water made from such a cold air-saturated water source often contains too much dissolved air gases that may slowly release the excess gases due to gas solubility change in response to temperature changes, forming numerous tiny gas bubbles on the surfaces of water chambers including the Al-Tf-Al membrane surface as was observed in one of the experiments. These tiny gas bubbles can sometimes become so problematic that they could negatively affect the formation and detection of localized protons on the Al-Tf-Al membrane surface because the gas bubbles apparently reside at the water-membrane interface and form an air-gap barrier between the membrane and the liquid water phase. For example, to eliminate this problem for improved reproducibility of the experiments, a special effort was made on the laboratory water source: the Millipore water was degassed by boiling the water through autoclave and then cooled down to room temperature before the experimental use.

Degassing of liquid water can be quickly accomplished also by use of a vacuum pump in conjunction with sonication of the liquid water. With the degassed liquid water, generation of an excess protons layer at a membrane-water interface has been experimentally demonstrated with high reproducibility. Alternatively, degassing can be solved by letting the liquid water to fully equilibrate with the laboratory temperature and air conditions for more than 10 days, during which liquid water can naturally (slowly) release the excess dissolved gases towards equilibration. Use of fully equilibrated liquid water which no longer generates any gas bubbles on membrane surface also produced good reproducible results.

Figure 2:
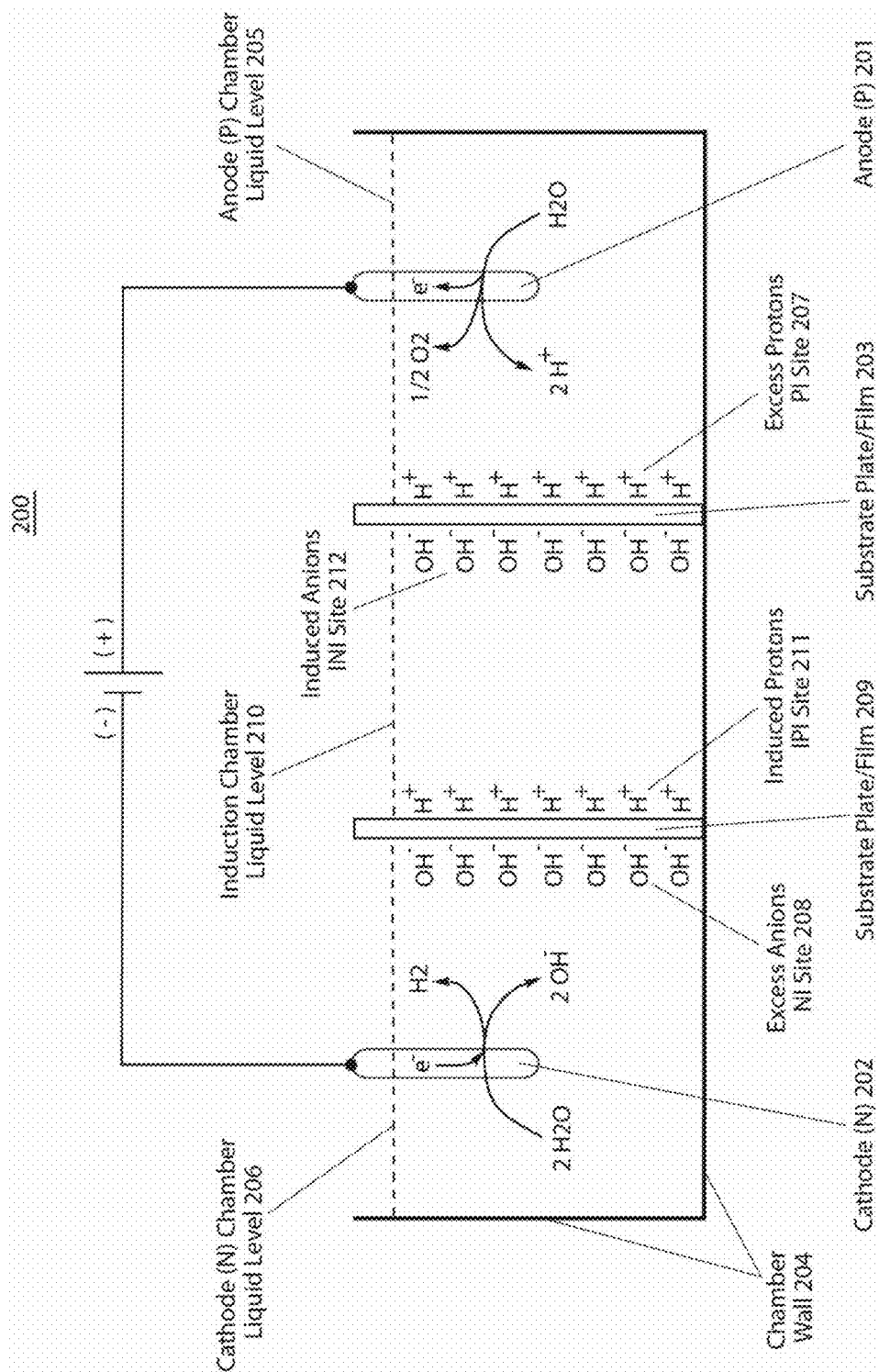
FIG. 2 presents a three-chamber system that produces excess protons and hydroxyl anions through an "open-circuit" water electrolysis process and results in two "excess protons-substrate-hydroxyl anions" capacitor-like structures for industrial applications.

Referring to FIG. 2, an excess proton production system 200 with three chambers is illustrated. The excess proton production system includes a substrate plate/film 203 placed in between an anode chamber 205 and an induction chamber 210 at the middle and another substrate plate/film 209 placed in between the induction chamber 210 and a cathode chamber 206. The chamber wall 204 is made of water impermeable and chemically-inert materials such as Teflon, plastic material, and glass, which are unreactive even if under high power voltage. The substrate plate/films (membranes) 203 and 206 joins with the chamber wall 204 using water-tight seal, resulting in the three separate chambers: the anode water chamber 205, the induction chamber 210, and the cathode water chamber 206. That is, the induction chamber 210 is formed in between the two substrate plate/films 203 and 209 which serve as its two end walls in conjunction with the wall 204 as its bottom and side walls.

According to one of the various embodiments, all the three chambers (from the left to the right: the cathode chamber, the induction chamber, and the anode chamber) are filled with pure water as shown in FIG. 2. The anode (N) chamber liquid level 205 is preferably set at the same level as the cathode (N) chamber liquid level 206 and at the induction chamber liquid level 210. Both the anode (P) 201 and cathode (N) 202 are typically made of stable electrode materials such as metallic platinum, palladium, gold, copper, certain stainless steel, graphite, and/or micro/nanometer carbon fibers. The excess protons and excess hydroxyl anions are generated in the anode and cathode water bodies through the use of "open-circuit" water-electrolysis by applying a direct current (DC) voltage across the anode (P) 201 and cathode (N) 202 electrodes. In accordance of the present invention, the excess protons produced by the "open-circuit" water-electrolysis process typically localize at the water-substrate interface (PI Site 207) along the surface of the plate/film (or membrane) where they electrostatically induce hydroxyl anions at the other side (INI Site 212) of the substrate plate, forming an "excess protons-plate-excess anions" capacitor-like structure. Similarly, the excess hydroxyl anions produced by the "open-circuit" water-electrolysis process localize at the water-substrate interface (NI Site 208) along the surface of the plate/film (or membrane) where they induce protons at the other side (IPI Site 211) of the substrate plate, forming another "excess protons-plate-excess anions" capacitor-like structure.

According to one of the various embodiments, the excess proton production system 200 (FIG. 2) can be operated in a manner similar to that of the excess proton production system 100 (FIG. 1) except that it can simultaneously treat two substrate plate/films 203 and 209.

Furthermore, according to one of the various embodiments, when necessary, certain chemicals such as sodium bicarbonate and potassium bicarbonate may be added into the induction chamber 210 to modulate (reduce) the effective concentration of the induced protons at the IPI site 211 by $Na^+$ (or $K^+$) cation exchange with the localized protons at the IPI site 211 to achieve more desirable results. In this way, the anode (P) chamber 205 and the cathode (N) chamber 206 can still work with pure water for production of excess protons and hydroxyl anions through the "open-circuit" water electrolysis process without the presence of any added chemicals that may interfere with the process.

The effective concentration of the electrostatically localized protons at the equilibrium of cation exchange can be calculated as:

$$[H_L^+] = \frac{[H_L^+]^0}{\prod_{i=1}^{n}\left\{K_{Pi}\left(\frac{[M_{pB}^{i+}]}{[H_{pB}^+]}\right)+1\right\}} \quad [6]$$

where $[H_L^+]^0$ is the effective concentration of localized protons without cation exchange. Here, $K_{Pi}$ is the equilibrium constant for non-proton cations ($M^{i+}$) to exchange for the localized protons at the water-membrane interface; $[M_{pB}^{i+}]$ is the concentration of the non-proton cations in the induction chamber liquid medium; and $[H_{pB}^+]$ is the proton concentration in the bulk phase of the induction chamber liquid medium.

Since protons have the smallest atomistic diameter and can exist as part of the water molecules, they can electrostatically distribute themselves to the water-membrane interface much more favorably than any other cations, such as $Na^+$, $Mg^{++}$ or $K^+$. Therefore, the equilibrium constant for protons to electrostatically occupy the cation sites at the water-membrane interface (in any possible competition with any other cations) is expected to be much larger than one. Certain cation exchange experimental studies (Lee et al., 2010 Environmental Science & Technology, 44(20):7970-7974; Skjemstad et al., 2008 Communications in Soil Science and Plant Analysis, 39(5-6):926-937) have recently indicated that the equilibrium constant for protons to exchange with other cations for cation binding sites can be on the order of $4.7 \times 10^{+6}$. Conversely, the equilibrium constant $K_{pi}$ for non-proton cations such as $Na^+$ to delocalize the localized protons from the membrane-water interface is in the order of $2.1 \times 10^{-7}$. Use of the cation exchange equilibrium constant $K_{Pi}$ can calculate the effective concentration of the localized excess protons using Equation 6 when non-proton cations are present, which is a parameter that may be helpful also to certain practitioners in accordance of the present invention.

Figure 3:
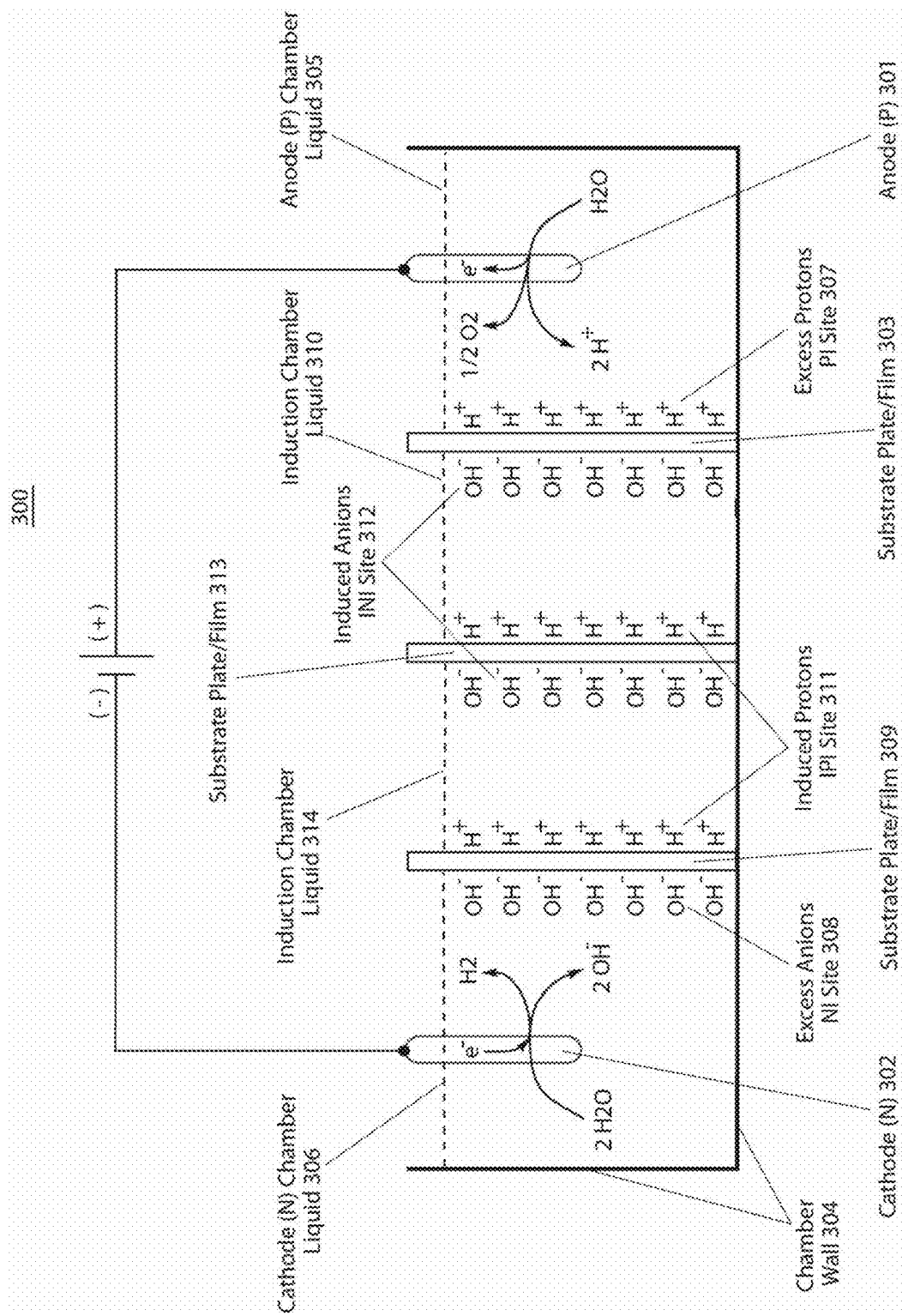
FIG. 3 presents a four-chamber system that produces excess protons and hydroxyl anions through an "open-circuit" water electrolysis process and results in three "excess protons-substrate-hydroxyl anions" capacitor-like structures for industrial applications.

Referring to FIG. 3, a four-chamber excess proton production and utilization system 300 is illustrated. The four-chamber system 300 includes three substrate plate/films 303, 309, and 313 that are placed in between an anode chamber 305 and a cathode chamber 305, forming additional two induction chambers 310 and 314 among the three substrate plate/films 303, 309, and 313. The chamber wall 304 is made of water impermeable and chemically-inert materials such as Teflon, plastic material, and glass, which are unreactive even if under high power voltage.

According to one of the various embodiments, all the four chambers (from the left to the right: the cathode chamber, the induction chambers 310 and 314, and the anode chamber) are filled with pure water as shown in FIG. 3. The anode (N) chamber liquid level 305 is set preferably at the same level as the cathode (N) chamber liquid level 306 and also at the same level as the induction chamber liquid level 313 and 310. Both the anode (P) 301 and cathode (N) 302 are typically made of stable electrode materials such as metallic platinum, palladium, gold, copper, certain stainless steel, graphite, micro/nanometer carbon fibers, and/or combination thereof. The excess protons and excess hydroxyl anions are generated in the anode and cathode water bodies through the use of "open-circuit" water-electrolysis by applying a direct current (DC) voltage across the anode (P) 301 and cathode (N) 302 electrodes (FIG. 3). The excess protons produced by the "open-circuit" water-electrolysis process localize at the water-substrate interface (PI Site 307) along the surface of the plate/film (or membrane) where they induce hydroxyl anions at the other side (INI Site 312) of the substrate plate, forming an "excess protons-plate-excess anions" capacitor-like structure. Similarly, the excess hydroxyl anions produced by the "open-circuit" water-electrolysis process localize at the water-substrate interface (NI Site 308) along the surface of the plate/film (or membrane) where they induce protons at the other side (IPI Site 311) of the substrate plate. As a result, two additional "excess protons-plate-excess anions" capacitor-like structures are formed.

According to one of the various embodiments, the excess proton production and utilization system 300 (FIG. 3) can be operated in a manner similar to that of the system 100 (FIG. 1) except that it can simultaneously treat three substrate plate/films 303, 209 and 313. Furthermore, certain chemicals such as sodium bicarbonate and potassium bicarbonate may be added into the induction chamber liquid 310 and 314 to modulate (reduce) the effective concentration of the induced protons at the IPI site(s) 311 by $Na^+$ (or $K^+$) cation exchange with the localized protons at the IPI site(s) 311 when such a modulation adjustment may become desirable in certain special applications.

According to one of the various embodiments, many more induction chambers can be used in between the anode chamber and the cathode chamber to simultaneously treat many substrate plate/films in a single system like the system 300 (FIG. 3). The number of induction chambers that can be used in between an anode chamber and a cathode chamber in a single excess protons and hydroxyl anions production and utilization system is selected from the group consisting of 0, 1, 2, 3, 4, 5, 6, 7, 8, 10, 11, 12, 13, 14, 15, 17, 18, 19, 20, 21, 22, 23, 24, 25, 26, 27, 28, 29, 30, 40, 50, 60, 70, 90, 100 and more. Consequently, the number of substrate plate/films that can be simultaneously treated in a single excess protons and hydroxyl anions production and utilization system is selected from the group consisting of 1, 2, 3, 4, 5, 6, 7, 8, 10, 11, 12, 13, 14, 15, 17, 18, 19, 20, 21, 22, 23, 24, 25, 26, 27, 28, 29, 30, 31, 41, 51, 61, 71, 81, 91, 101, and more. These selections may be used in part and/or in any combinations depending on the value of water electrolysis voltage and the effective concentration of localized excess protons that may be required for a given processing treatment application.

Figure 4:
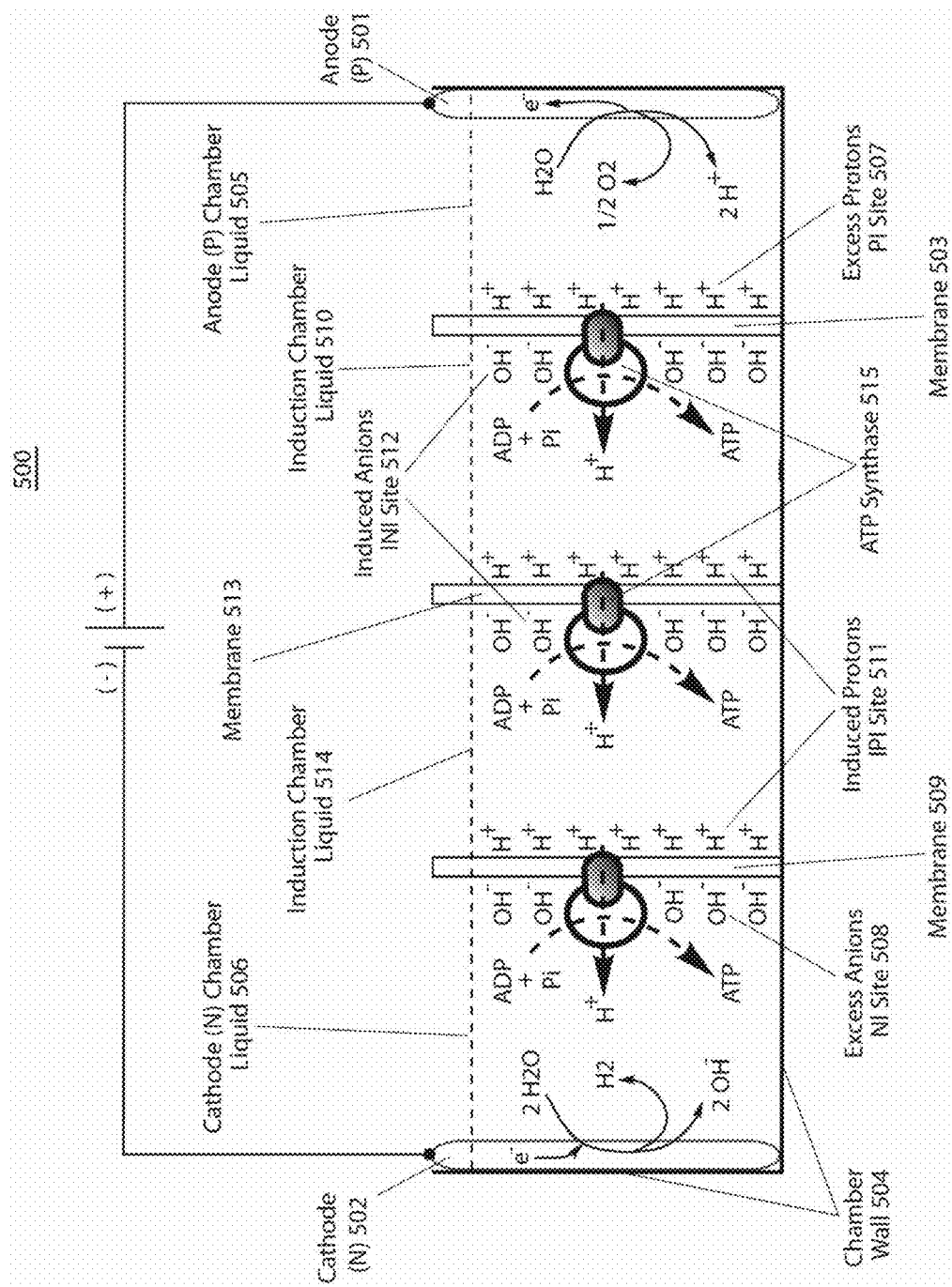
FIG. 4 presents a multi-chamber system that produces excess protons and hydroxyl anions forming multiple "excess protons-membrane-hydroxyl anions" capacitor-like structures for extraction of latent heat molecular motion energy to generate additional protonic motive force (equivalent to Gibbs free energy) to do useful work such as driving ATP synthesis.

Referring to FIG. 4, a multi-chamber excess proton production and utilization system 500 is illustrated. The multi-chamber system 500 comprises: three (more or multiple) membranes 503, 509, and 513 that are placed in between an anode chamber 505 and a cathode chamber 506, forming additional two (more or multiple) induction chambers 510 and 514 among the three (more or multiple) membranes 503, 509, and 513. The chamber wall 504 is made of water impermeable and chemically-inert materials such as Teflon, plastic material, and glass, which are unreactive even if under high power voltage. There are proton users such as ATP synthase 515 that are embedded with each of the three (more or multiple) membranes 503, 509, and 513 that mimic a biological membrane.

According to one of the various embodiments, the "excess protons-membrane-hydroxyl anions" capacitor-like structures may be employed to enable novel utilization of low-grade heat energy from the ambient temperature environment such as the latent heat energy associated with the molecular thermal motion of the localized protons to perform useful work such as driving the synthesis of ATP (FIG. 4). Typically, this special energy technology process includes the following steps and features: a) through use of the "open-circuit" water-electrolysis process, excess protons are generated in anode liquid chamber 505 while excess hydroxyl anions are created in cathode liquid chamber 506; b) the generated excess protons electrostatically localize themselves primarily along the water-membrane interface at the PI site 507 while the excess anions electrostatically localize themselves primarily along the water-membrane interface at the NI site 508; c) the excess protons at PI site 507 in conjunction with the excess anions at NI site 508 electrostatically induce the formation of the induced anions at INI site(s) 512 and the induced protons at IPI site(s) 511 in the induction liquid chambers 510 and 514; d) The formation of the electrostatically localized protons layer constitutes a type of "negative entropy" event during the formation of multiple "localized protons-membrane-anions" capacitor-like structures; e) the formation of multiple "localized protons-membrane-anions" capacitor-like structures results in the formation of membrane potential across each of the membranes; f) In addition to the generation of membrane potential, significant amount of "bonus" local proton motive force (useful Gibbs free energy) is created also from the "entropy effect" of the localized protons since their thermal motions (latent heat) possibly including their Brownian motion can drive nanometer-scale molecular machines such as $F_0F_1$-ATP synthase embedded in the membrane; g) Utilization of the total proton motive force (the membrane potential and the local proton motive force) from the localized protons at PI site and IPI site(s) to do work as the protons flow across each of the membranes through the membrane-embedded ATP synthase 515 in driving ATP synthesis from ADP and Pi (inorganic phosphate); and h) the molecular hydrogen (H2) and oxygen (O2) gas products are collected at the cathode and the anode, respectively.

According to one of the various embodiments, it is a preferred practice to place the proton-generating anode electrode well into the bulk phase liquid and to keep the mouths of proton users such as ATP synthase 515 being located rightly within the localized excess protons layer along the membrane surface as illustrated in FIG. 4, for the best effect to utilize latent heat associated with the thermal motion energy of localized protons to perform useful work such as driving the synthesis of ATP in accordance with the present invention.

The well-established scientific knowledge that proton motive force (pmf) is equivalent to Gibbs free energy ($\Delta G = -n \cdot F \cdot pmf$, where n is proton charge and F is Faraday constant) that can be employed to do useful work as in the example of driving ATP synthesis is one of the fundamentals in the present invention. It is known that ATP represents a form of chemical energy that can be used not only in living organisms but also in certain industrial biochemical engineering processes for making certain biomolecules such as nucleic acids and other compounds of importance including certain pharmaceutical-related products.

According to one of the various embodiments, the total proton motive force (pmf) across a biological membrane and/or a bio-inspired synthetic membrane taking into account the surface localized protons can be expressed as $$pmf = \Delta\psi + \frac{2.3RT}{F}\log_{10}(\{[H_L^+] + [H_{pB}^+]\}/[H_{nB}^+]) \qquad [7]$$

Here $\Delta\psi$ is the electrical potential difference across the membrane, R is the gas constant, T is the absolute temperature, F is Faraday's constant, $[H_L^+]$ is the concentration of surface localized protons, $[H_{pB}^+]$ is the proton concentration in the periplasmic bulk aqueous phase (equivalent to the anodic chamber liquid of FIG. 1c), and $[H_{nB}^+]$ is the proton concentration in the cytoplasmic bulk phase (equivalent to the cathodic chamber liquid in FIG. 1c).

This pmf expression may be rewritten to isolate the latent heat thermal molecular motion energy contribution due to the localized protons as follows:

$$pmf = \qquad [8]$$
$$\Delta\psi + \frac{2.3RT}{F}\log_{10}([H_{pB}^+]/[H_{nB}^+]) + \frac{2.3RT}{F}\log_{10}(1 + [H_L^+]/[H_{pB}^+])$$

The first two terms of Eq. 8 comprise the "classic" expression for the proton motive force (pmf) used in textbooks (Nicholls and Ferguson, Bioenergetics (Fourth Edition). 2013, Academic Press: Boston. p. 27-51; Skulachev, Bogachev, and Kasparinsky, Principles of Bioenergetics. 2012: Springer Berlin Heidelberg) and the third term is the local pmf component from the localized protons that may be employed as a special tool to extract thermal molecular motion energy (latent heat) to create useful Gibbs free energy to do work according to one of the various embodiments in accordance of the present invention.

For certain industrial applications, the bulk phase liquid pH (i.e., the bulk liquid phase proton concentrations) can be set to be the same. For example, a liquid medium such as pure water (pH 7.0), air-equilibrated water (pH 5.8) or a pH-buffered reaction medium can be used at the same pH for each of the all liquid chambers as shown in the example of FIG. 4. According to one of the various embodiments, the creation of excess protons does not significantly alter the bulk liquid phase proton concentration in any of the liquid chambers since excess protons do not stay in the bulk liquid phase and they electrostatically localize primarily at the water-membrane interface associated with the dominant capacitance there. This prediction has now been verified experimentally by the measurements of the bulk liquid phase pH and by the detection of the localized protons detection with proton-sensing Al films. Therefore, under this special condition, the second term of Eq. 8 can be practically treated as zero and the total pmf value may be calculated practically by using of the first term (membrane potential) and the third term (local pmf).

For some special industrial applications, certain salt solutions and/or buffer solutions may be employed in any of the liquid chambers (as shown in FIG. 4) to modulate the total pmf values. The effective concentration of the electrostatically localized protons at the equilibrium of cation exchange can be calculated according to Eq. 6, which may then be used in calculating the pmf value with Eq. 8.

Table 2 lists the exemplary pmf values calculated using Eqs. 6-8 across a mimicked biological membrane with a specific membrane capacitance per unit surface area (C/S) of 13.2 mf/m$^2$ and a reasonable thinness of the localized proton layer (l) of 1 nm with an exemplary physiological liquid medium. The exemplary physiological liquid medium comprises the following cations: 300 mM Na$^+$, 3.584 mM K$^+$, 0.1 mM Mg$^{++}$, 0.4557 mM Ca$^{++}$, 38.08 µM Zn$^{++}$, 25.17 µM Fe$^{++}$, 5.557 µM Mn$^{++}$, 1.602 µM Cu$^{++}$, 0.859 µM Co$^{++}$, and 0.971 µM NH$_4^+$. The equilibrium constants $K_{Pi}$ of cation exchange with localized protons used in this calculation were estimated from preliminary experimental data: 7.41×10$^{-8}$ and 2.48×10$^{-8}$ for Na$^+$ and K$^+$. The average of these two (4.95×10$^{-8}$) was used to estimate for $K_{Pi}$ of the other monovalent cation NH$_4^+$. The $K_{Pi}$ value of 2.1×10$^{-7}$ for divalent cation Mg$^{++}$ was calculated from the experimental data of cation exchange studies (Lee et al. 2010 Environmental Science & Technology, 44(20): 7970-7974; Skjemstad et al., 2008 Communications in Soil Science and Plant Analysis, 39(5-6): 926-937) and was used for the other divalent cations here as well.

TABLE 2

Calculated pmf values across a mimicked biological membrane with a specific membrane capacitance per unit surface area (C/S) of 13.2 mf/m² and a reasonable thinness of the localized proton layer (l) of 1 nm under a simulated physiological salt solution using Eqs. 6-8 at the temperature T = 298 K. The "local" pmf is the last term in Eq. 8 due to the localized protons, while the first two terms of Eq. 8 give the "classic" pmf.

| $pH_{pB}$ | $pH_{nB}$ | $\Delta\psi$ (mV) | $[H_L^+]^0$ (molar) | Exchange reduction factor | $[H_L^+]$ (molar) | Local pmf (mV) | Classic pmf (mV) | Total pmf (mV) |
|---|---|---|---|---|---|---|---|---|
| 8.2 | 8.2 | 25  | $3.42 \times 10^{-3}$ | 4.683 | $7.30 \times 10^{-4}$ | 299 | 25  | 324 |
| 8.2 | 8.2 | 50  | $6.84 \times 10^{-3}$ | 4.683 | $1.46 \times 10^{-3}$ | 317 | 50  | 367 |
| 8.2 | 8.2 | 100 | $1.37 \times 10^{-2}$ | 4.683 | $2.92 \times 10^{-3}$ | 335 | 100 | 435 |
| 8.2 | 8.2 | 150 | $2.05 \times 10^{-2}$ | 4.683 | $4.38 \times 10^{-3}$ | 345 | 150 | 495 |
| 8.2 | 8.2 | 200 | $2.74 \times 10^{-2}$ | 4.683 | $5.48 \times 10^{-3}$ | 352 | 200 | 552 |
| 7.0 | 7.0 | 200 | $2.74 \times 10^{-2}$ | 1.225 | $2.23 \times 10^{-2}$ | 316 | 200 | 516 |
| 7.0 | 7.0 | 150 | $2.05 \times 10^{-2}$ | 1.225 | $1.68 \times 10^{-2}$ | 309 | 150 | 459 |
| 7.0 | 7.0 | 100 | $1.37 \times 10^{-2}$ | 1.225 | $1.12 \times 10^{-2}$ | 298 | 100 | 398 |
| 7.0 | 7.0 | 50  | $6.84 \times 10^{-3}$ | 1.225 | $5.58 \times 10^{-3}$ | 280 | 50  | 330 |
| 7.0 | 7.0 | 25  | $3.42 \times 10^{-3}$ | 1.225 | $2.79 \times 10^{-3}$ | 263 | 25  | 288 |
| 5.8 | 5.8 | 25  | $3.42 \times 10^{-3}$ | 1.014 | $3.37 \times 10^{-3}$ | 197 | 25  | 222 |
| 5.8 | 5.8 | 50  | $6.84 \times 10^{-3}$ | 1.014 | $6.73 \times 10^{-3}$ | 214 | 50  | 264 |
| 5.8 | 5.8 | 100 | $1.37 \times 10^{-2}$ | 1.014 | $1.35 \times 10^{-2}$ | 232 | 100 | 332 |
| 5.8 | 5.8 | 150 | $2.05 \times 10^{-2}$ | 1.014 | $2.02 \times 10^{-2}$ | 243 | 150 | 393 |
| 5.8 | 5.8 | 200 | $2.74 \times 10^{-2}$ | 1.014 | $2.70 \times 10^{-2}$ | 250 | 200 | 450 |

The results listed in Table 2 demonstrate that the "local" pmf (equivalent to Gibbs free energy) extracted from the latent heat with localized protons as calculated from the third term of Eq. 8 is a very significant component of the total pmf. With a membrane potential of 50 mV and liquid bulk phase pH 7, the "local" pmf extracted from the latent heat with localized protons is 280 mV, which represents nearly 85% of the total pmf (330 mV). Similarly, with a membrane potential of 25 mV and liquid bulk phase pH 7, the "local" pmf extracted from latent heat with the localized protons is 263 mV, which represents as much as 91% of the total pmf (288 mV) and is more than sufficient to drive ATP synthesis that requires a minimal pmf of 116 mV. Therefore, these results demonstrate that the innovative application of localized excess protons in accordance with the present invention may provide a special novel energy technology process function to extract latent heat including the molecular thermal motion energy associated with localized protons at ambient environmental temperature for generating local proton motive force (equivalent to Gibbs free energy) to do useful work such as driving ATP synthesis.

The results shown in Table 2 (the "local" pmf of 263 mV extracted from latent heat with localized protons with a membrane potential of 25 mV) can also help to elucidate the mystery of how a hyperthermophilic archaeon (*Thermococcus onnurineus* NA1) could grow by the anaerobic oxidation of formate to CO2 and H2, which has very little free energy change at its physiological conditions ($\Delta G^0=-2.6$ kJ/mol) (Lim et al., 2014 Proceedings of the National Academy of Sciences, USA 111(31):11497-11502). If this free energy ($\Delta G^0=-2.6$ kJ/mol) is utilized to drive formation of an electrochemical proton gradient across the membrane, it could possibly form a membrane potential of about 25 mV, which, if based on the delocalized proton view of Peter Mitchell's Chemiosmotic Theory, would translate to a classic pmf of only 25 mV that would not be sufficient to drive ATP synthesis to support cell growth. On the other hand, based on the data presented in Table 2 of the present invention, a membrane potential of 25 mV may translate to a total pmf of 288 mV with a local pmf (263 mV) generated from latent heat molecular motion energy of the localized protons, which is sufficient to drive ATP synthesis to support cell growth (possibly also involving a Na+/H+ antiporter in the cell). Therefore, that difficult bioenergetics question associated with *Thermococcus onnurineus* NA1 may now be answered satisfactorily by the special energy-transduction mechanism of localized protons in extracting latent heat molecular motion energy to generate a local pmf as much as 263 mV as disclosed herein.

The data in Table 2 also show that at a membrane potential of 200 mV with the same pH neutral liquid media, the "local" pmf extracted from latent heat is 316 mV which is 61% of the total pmf (516 mV). This result indicates that at a high membrane potential (200 mV), its effect on enhancing "local" pmf can become limited. Therefore, according to one of the various embodiments, it is a preferred practice to employ a relatively smaller membrane potential as long as it can still electrostatically hold the excess protons at the water membrane interface to extract the latent heat energy to generate the "local" pmf, yielding a better ratio of local pmf to total pmf.

According to one of the various embodiments, the special energy technology process for generating useful Gibbs free energy from utilization of molecular thermal motion energy associated with localized protons has a special feature that its local proton motive force (pmf) generated from its special utilization of latent heat energy may be calculated according to the following formula:

$$\text{Local } pmf = \frac{2.3RT}{F}\log_{10}(1 + [H_L^+]/[H_{pB}^+]) \quad [9]$$

Where R is the gas constant, T is the absolute temperature, F is Faraday's constant, $[H_L^+]$ is the concentration of surface localized protons, and $[H_{pB}^+]$ is the proton concentration in the anode bulk aqueous phase.

With this Equation [9], it is now, for the first time, clearly expressed that the local pmf is a logarithmic function of the ratio of localized proton concentration $[H_L^+]$ at the liquid-membrane interface to the delocalized proton concentration $[H_{pB}^+]$ in the liquid bulk phase at the same side of the membrane (but not to the delocalized proton concentration

[$H_{nB}^+$] in the cathodic chamber liquid at the other side of the membrane). It is the electrostatic proton localization that brings the excess protons to the water-membrane interface that enables the special utilization of molecular thermal motion energy from the ambient temperature environment to create proton motive force without being constrained by the Second Law of Thermodynamics. Therefore, this also represents a breakthrough in the fundamental understanding of energy transduction and energy recycle and utilization, which may have seminal scientific and practical implications for energy and environmental sustainability on Earth.

Furthermore, from Eq. 9 in conjunction with Eq. 6, it is understood that when a significant amount of cations such as $Na^+$ occupy the localized proton layer by cation exchange as in the case with high salt concentrations, it may form a localized sodium ion ($Na^+$) concentration [$Na_L^+$] while reducing the concentration of localized protons [$H_L^+$]. Consequently, in the presence of high sodium ion ($Na^+$) concentration [$Na_{pB}^+$] in liquid bulk phase, certain amounts of local pmf may be converted to local sodium motive force (smf) through cation exchange with the localized protons. The value of local smf may be calculated as:

$$\text{Local } smf = \frac{2.3RT}{F}\log_{10}(1 + [Na_L^+]/[Na_{pB}^+]) \quad [10]$$

Therefore, according to one of the various embodiments, application of excess protons in the presence of high sodium cation ($Na^+$) concentration [$Na_{pB}^+$] in liquid bulk phase may be used to generate local smf also from the special utilization of latent heat energy from the ambient temperature environment to do useful work such as driving an A1Ao-ATP Synthase for ATP Synthesis (McMillan et al., 2011 Journal of Biological Chemistry, 286(46):39882-39892). Therefore, exemplary embodiments may be extended to other localizable cations and other species such as $Na^+$, $K^+$, $Li^+$, $Rb^+$, $Cs^+$, $Co^{++}$, $Ni^{++}$, $Zn^{++}$, $Cu^{++}$, $Fe^{++}$, $Mn^{++}$, $Ca^{++}$, and/or $Mg^{++}$ for various industrial applications including the special extraction of latent heat molecular thermal motion energy for energy technology applications.

According to one of the various embodiments, it is a preferred practice to employ multiple membranes, of which each is with a relatively smaller membrane potential, in a multi-chamber system such as that illustrated in FIG. 4 that can be employed with use of a relatively small electrolysis voltage for generating excess protons to extract latent heat molecular thermal motion energy to create a total pmf value much larger than the input electrolysis voltage. The extracted molecular thermal motion energy in the form of pmf from the latent heat of ambient temperature environment may be utilized to drive nanometer machines such as ATP synthase, proton-driven molecular transport systems and enzymes to perform useful work.

According to one of the various embodiments, depending on a given specific application and its associated temperature conditions, liquid media compositions, and the properties of proton users and membrane material such as its thickness, proton capacitance and other physical chemistry properties, the number of membranes that may be used per multi-chamber system as illustrated in FIG. 4 for the purpose of extracting latent heat to create local pmf may be selected from the group consisting of 1, 2, 3, 4, 5, 6, 7, 8, 8, 9, 10, 20, 30, 40, 50, 60, 70, 80, 90, 100, 200, 300, 500, 1000, 2000, 5000, 10,000, 100,000, 1,000,000, more and/or within a range bounded by any two of these values.

According to one of the various embodiments, depending on a given specific application and its associated temperature conditions, liquid media compositions, and the properties of proton users and the membrane material such as its thickness, proton capacitance and other physical chemistry properties, the membrane potential for the purpose of extracting latent heat to create local pmf may be selected from the group consisting of 0.1 mV, 0.5 mV, 1 mV, 5 mV, 10 mV, 15 mV, 20 mV, 25 mV, 30 mV, 40 mV, 50 mV, 60 mV, 70 mV, 80 mV, 90 mV, 100 mV, 110 mV, 120 mV, 130 mV, 140 mV, 150 mV, 200 mV, 250 mV, 300 mV, 500 mV, 1000 mV, 2 V, 5V, 10 V, 20 V, 50 V, 100 V, 200 V, 300 V, 500V, 1000V and/or within a range bounded by any two of these values.

According to one of the various embodiments, depending on a given specific application and its associated temperature conditions, liquid media compositions, and the properties of proton users and the membrane material such as its thickness, proton capacitance and other physical chemistry properties, the said special energy technology process to extract latent heat molecular thermal motion energy associated with localized protons for generating local proton motive force (equivalent to Gibbs free energy) may be operated in a wide range of temperatures including ambient temperatures, elevated temperatures, and/or low temperatures.

The results listed in Table 2 showed that the "local" pmf extracted from the latent heat with localized protons at neutral pH or slightly alkaline bulk liquid can be somewhat bigger than that at acidic conditions at the same membrane potential and liquid media ionic strength. For example, at the membrane potential of 100 mV, the amounts of "local" pmf with liquid bulk phase pH 8.2 and 7.0 are 335 and 298 mV, both is bigger than that (232 mV) with liquid bulk phase pH 5.8. Therefore, according to one of the various embodiments, it is a preferred practice to employ neutral or slightly alkaline bulk liquid pH to better generate the "local" pmf (Gibbs free energy).

As shown in Table 2, the liquid media with pH 5.8, 7.0, and 8.2 practically all work very well with the excess protons-based energy technology to generate "local" pmf in utilizing the latent heat energy which is conventionally thought as impossible to be used from ambient temperature environment. Depending on a given specific application and its associated temperature conditions, liquid media compositions including the ionic strength, the properties of proton users, the membrane material such as its thickness, proton capacitance and other physical chemistry properties, the pH of liquid media may however be from selected the group consisting of pH 1, 2, 3, 4, 5, 6, 6.5, 7.0, 7.5, 8.0, 8.5, 9.0, 9.5, 10, 10.5, 11, 11.5, 12, 13, 14 and/or within a range bounded by any two of these values in accordance with one of the various embodiments of the present invention.

Meanwhile, the data also indicate that at liquid bulk phase pH 8.2, the exchange reduction factor (4.683) gets significantly bigger than those (1.225 and 1.014) with bulk liquid pH 7.0 and 5.8, which could negatively impact the localized proton concentration. Therefore, according to one of the various embodiments, it is also a preferred practice to employ pure deionized water or low salt liquid media to more effectively generate "local" pmf (equivalent to Gibbs free energy) from latent heat molecular motion energy, although high salt solution can also be employed when the liquid pH is not high such as above pH 12.

One of the key fundamental features in the present invention is the utilization of latent heat with localized protons to recycle/utilize the fully dissipated waste heat energy, which conventionally is thought to be totally unusable, to generate local pmf to do useful work. This essentially provides a high innovative method to renew the totally "dead" latent heat energy in ambient temperature environment that according to the Second Law of Thermodynamics would be completely unusable. That is, the "dead" latent heat energy can now be reborn to create new Gibbs free energy in the form of local pmf in accordance with the present invention. Therefore, it fundamentally represents a special energy-recycle and energy-renew technology.

Furthermore, it is the effective localized protons concentrations and their associated local pmf (Gibbs free energy) that fundamentally also enables the industrial applications of treating substrate materials including the protonation of certain synthetic polymer films and proton-etching of substrate metal plates. Therefore, the useful work that can be done with local pmf (Gibbs free energy) includes the local pmf-driven protonation of certain protonatable synthetic polymer films and the proton-driven oxidation of certain substrate metal atoms for the industrial applications, in addition to the well-known pmf utilization for driving synthesis of ATP useful not only in living organisms but also in certain industrial biochemical engineering applications.

Therefore, exemplary embodiments provide a series of comprehensive methods for creating effective localized excess protons concentrations with a special excess proton production and utilization system including the use of an open-circuit water electrolysis process with a pair of anode and cathode electrodes in a special liquid membrane chamber system forming and using excess protons associated with an excess protons-membrane-anions capacitor-like system to enable a series of special energy recycle-related technology process functions with utilization of latent heat energy for various special industrial applications including: a) utilization of latent heat molecular thermal motion energy for energy recycling and renewing of the fully dissipated waste heat energy in ambient temperature environment, which conventionally is thought to be totally unusable, to generate local proton motive force equivalent to Gibbs free energy to do useful work; b) treatment comprising protonation and proton-etching of a substrate material plate/film by forming and utilizing excess protons associated with an excess protons-membrane-hydroxyl anions capacitor-like system; and c) production and conversion of local excess protons proton motive force to the other ion motive force (equivalent to Gibbs free energy) for a series of other cation species for utilization of latent heat molecular thermal motion energy and other industrial applications selected from the group consisting of $Na^+$, $K^+$, $Li^+$, $Rb^+$, $Cs^+$, $Co^{++}$, $Ni^{++}$, $Zn^{++}$, $Cu^{++}$, $Fe^{++}$, $Mn^{++}$, $Ca^{++}$, $Mg^{++}$, and combinations thereof.

EXAMPLES

The following examples to illustrate embodiments of how the compositions and methods described herein are made and evaluated, and are intended to be purely exemplary and are not intended to limit the scope of the invention.

Example 1

Localized Excess Protons Demonstrated with a Proton-Sensing Film

The excess proton production and utilization system 100 (as illustrated in FIG. 1) has recently been experimentally demonstrated in the Lee laboratory at ODU, using an "open-circuit" water electrolysis process and resulted in the formation of an "excess protons-substrate-hydroxyl anions" capacitor-like system. During the open-circuit electrolysis of pure water, excess protons were produced in the anode chamber while excess hydroxyl anions were generated in the cathode chamber.

Figure 5:
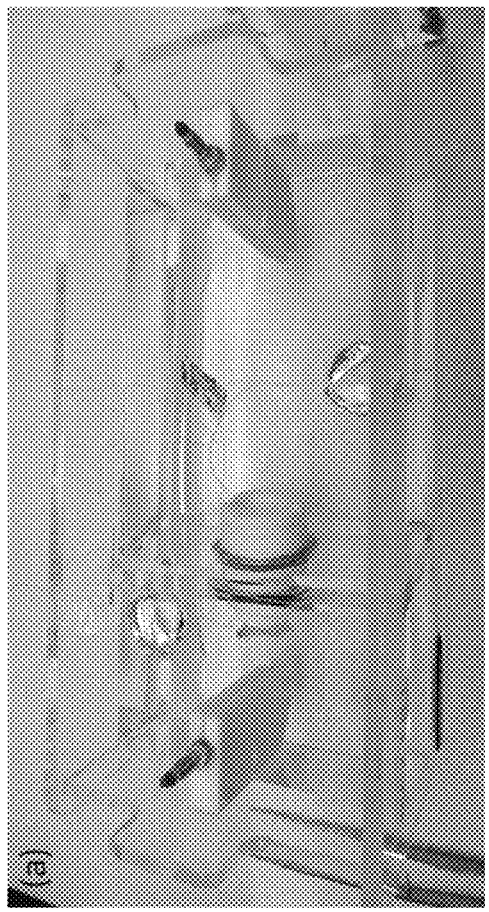
FIG. 5 presents: (a) A top view photograph showing the ElectroPrep apparatus. Pieces of proton-sensitive films were applied on the water surface and in the middle (bulk phase) of both the anode and cathode water chambers. Nylon strings were used to anchor the pieces of proton-sensitive films that were suspended in the middle of both the anode and cathode water chambers. (b) polytetrafluoroethylene, e.g., Teflon, center chamber assembly with a Tf-Al-Tf membrane. (c) polytetrafluoroethylene, e.g., Teflon, center chamber assembly with a proton-sensing Al-Tf-Al membrane.
Figure 5:
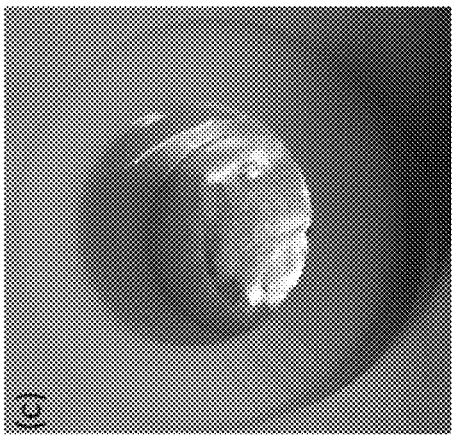
Figure 5:
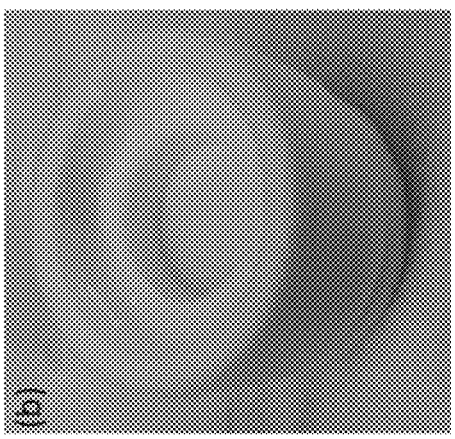

It is known that aluminum surface can begin to be corroded by protons when the effective proton concentration is above 0.1 mM (equivalent to a pH value of below 4) (Pourbaix 1974 Corrosion Science, 14(1): 25-82). This property was therefore employed as a proton-sensing mechanism in combination with the bulk phase pH electrode measurement to determine the distribution of excess protons in the water-membrane-water system (FIG. 1). In the first set of experiments (performed in triplicate), small pieces of aluminum film were employed as a proton sensor at a number of locations in both of the water chambers to serve as an indicator for the excess protons. As illustrated in FIGS. 1 and 5, a Teflon membrane (Tf) was sandwiched in between two pieces of aluminum film (Al), forming a proton-sensing Al-Tf-Al membrane system that separate the two water bodies: the cathode water body on the left and the anode water body on the right.

Figure 6:
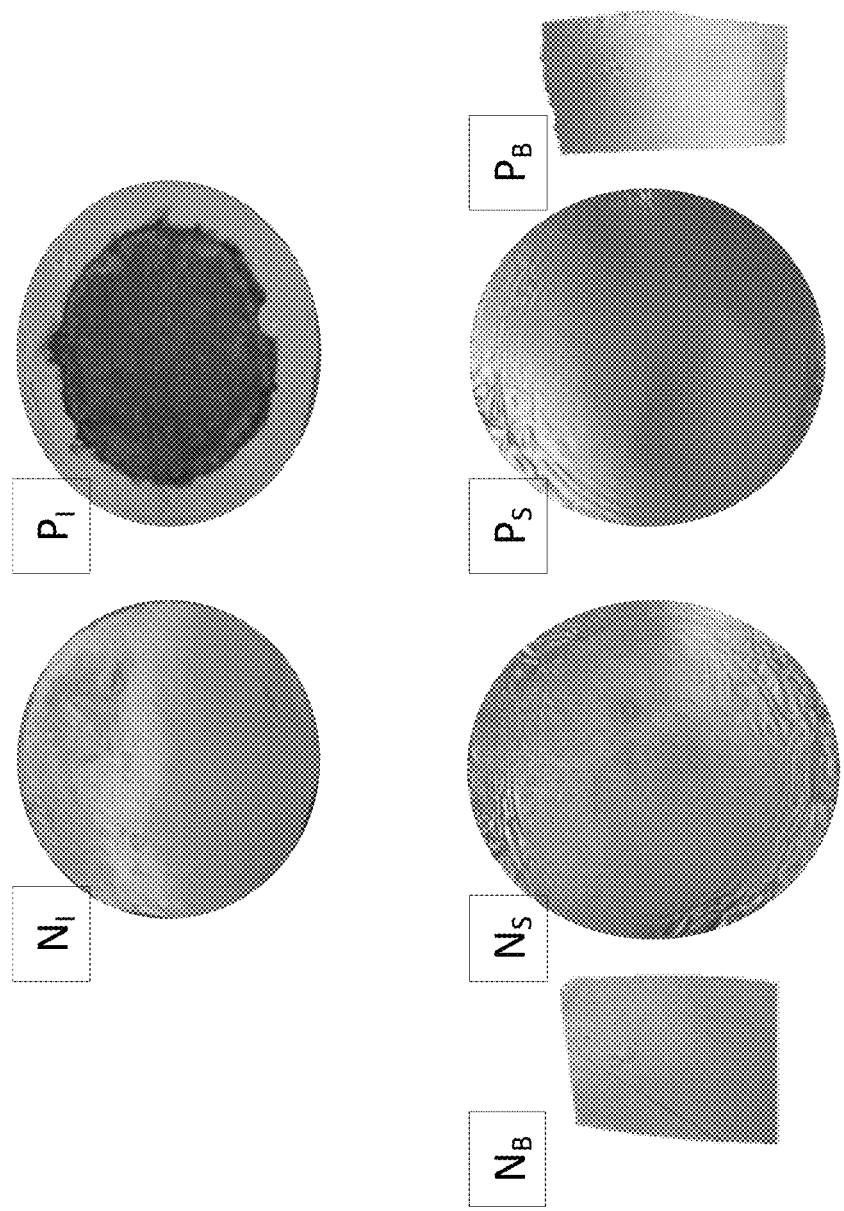
FIG. 6 presents the observations with proton-sensing Al films after 10 hours of cathode water Al-Tf-Al water anode experiment with water electrolysis (200 V). $N_f$: Proton-sensing film at the N side of Teflon membrane detected no proton activity. $P_f$: Proton-sensing film at the P side of Teflon membrane detected dramatic activity of localized protons (dark grey color). $N_B$: Proton-sensing film suspended inside the water of the cathode chamber. $N_S$: Proton-sensing film floating on the water surface of cathode chamber. $P_S$: Proton-sensing film floating on the water surface of anode chamber. $P_B$: Proton-sensing film suspended inside the water of the anode chamber.

The result of the "cathode water Al-Tf-Al water anode" experiment showed that only the proton-sensing film placed at the $P_I$ site facing the anode liquid showed proton-associated corrosion (see the dark brownish grey on the exposed part of the proton-sensing film in FIG. 6) while the proton-sensing film placed in the bulk liquid phase ($P_B$) of the anode chamber or floated on the top surface ($P_S$) of the anode water body showed no proton-associated corrosion activity (FIG. 5*a*). This is a significant observation since it indicates that excess protons are indeed localized primarily along the water-membrane interface at the $P_I$ site, but not in the bulk liquid phase ($P_B$). Also as expected, all pieces of proton-sensing film placed at the $N_I$, $N_B$, and $N_S$ sites of the cathode liquid showed no proton-associated corrosion activity as well.

According to the Mitchellian proton delocalized view, the excess protons in a water body would behave like a solute such as a sugar molecule which can stay anywhere in the liquid including its bulk liquid phase. Certain commonly heard arguments in favor of the Mitchellian proton delocalized view even as of today seem still believe that the excess protons would behave like solutes that could delocalize into the bulk liquid phase somehow by "proton solvation" or "electro diffusion". If that delocalized view is true, it would predict that all the proton-sensing films in the anode water chamber including the one placed in the bulk liquid ($P_B$) should be able to detect the excess protons. The observation that the proton sensor placed into the anode chamber bulk water phase ($P_B$) could not detect any excess protons while the proton sensor placed at the $P_I$ site showed dramatic proton-associated aluminum corrosion activity clearly rejects the Mitchellian proton delocalized view. The result clearly demonstrated the formation of localized excess protons at the water-substrate (proton-sensing Al film) interface as outlined in the present invention.

Example 2

Characterization of Excess Protons with Bulk-Phase pH Measurements

During a 10-hour experiment with 200V-driven water electrolysis, it was noticed, as expected, that the formation of small gas bubbles at both the anode and cathode platinum electrodes. This observation is consistent with the well-known water electrolysis process in which water is electrolytically oxidized to molecular oxygen (gas) producing protons in the anode water compartment while protons are reduced to molecular hydrogen (gas) leaving more hydroxyl anions in the cathode water compartment. If the Mitchellian proton delocalized view is true, it would predict that the production of excess protons in the anode water compartment would result in a lower pH value for the bulk water body while the generation of excess hydroxyl anions in the cathode water body would result in a higher pH in its bulk water body. That is, if the proton delocalized view is true, it would predict a significant bulk-phase pH difference (ΔpH) between the anode and the cathode water bodies. The experimental result with the bulk-phase pH measurements demonstrated that the Mitchellian proton delocalized view is not true. As shown in Table 3, after the 10-hour experiment with the water Al-Tf-Al (membrane) water system, the measured pH value in the anode bulk water body (5.76±0.09) remained essentially the same as that of the cathode bulk water phase (5.78±0.14). These bulk water phase pH values averaged from 3 replication experiments (each replication experiment with at least 6 reading of pH measurement in each chamber water, n=3×6=18) were statistically also the same as those (5.78±0.04 and 5.76±0.02) in the control experiments in absence of the water electrolysis process. This is a significant experimental observation since it confirmed that the excess protons indeed do not stay in the bulk water phase and thus cannot be measured by a pH electrode in the bulk phase.

This observation can also explain why in certain bioenergetic system such as thylakoids where ATP synthesis through photophosphorylation sometimes can occur without measurable ΔpH across the thylakoid membrane between the two bulk aqueous phases (Vinkler, Avron, Boyer 1978 FEBS Letters 96(1): 129-134). As shown in the present study, although the bulk-phase pH difference (ΔpH) between the anode chamber water and the cathode chamber water is zero, the excess protons were localized at the water-membrane interface as demonstrated by the dramatic proton activity of the proton-sensing film placed at the $P_I$ site (FIG. 6). This indicated that the concentration of localized excess protons was much higher than 0.1 mM (equivalent to a pH value of well below 4).

Figure 8A:
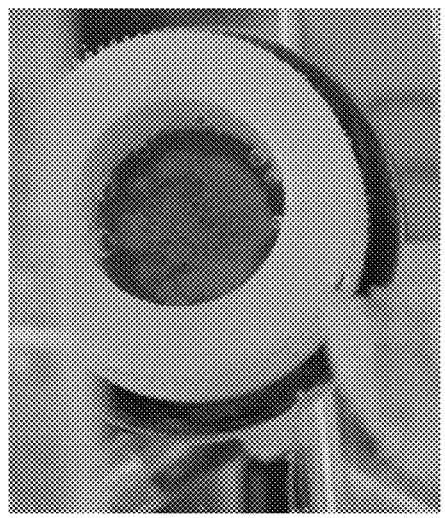
FIG. 8a presents a photograph showing the Teflon center chamber with the Al-Tf-Al membrane (at the $P_I$ site) seen through the anode chamber water after the 10-hour experiment with generation of excess protons through water electrolysis. Formation of gas bubbles and significant localized proton activity was noticed on the aluminum membrane surface at the $P_I$ site.
Figure 8B:
FIG. 8b presents a photograph showing the ElectroPrep electrolysis system after 10-hour water electrolysis. Notice, the proton-sensing Al film held in the bulk water phase ($P_B$) near the middle of the anode chamber (right) showed no excess proton activity during the entire 10-hour experiment. The bulk water phase pH was measured by inserting the probe into the anode (right side) and cathode (left side) chambers.

Furthermore, the measured pH value of 5.76±0.09 in the anode bulk water phase was also consistent with the observation that the piece of proton-sensing film placed in the anode bulk water phase ($P_B$) showed no sign of proton-associated corrosion (oxidation by the excess protons) activity (FIG. 6 $P_B$ and FIG. 8b) while the proton-sensing film placed at $P_I$ site had dramatic proton-associated corrosion (FIG. 6$P_I$). This indicated that the generated excess protons are indeed localized primarily at the water-membrane interface at the $P_I$ site resulting in a proton surface density that is high enough (equivalent to a pH value well below 4) to cause the aluminum corrosion there.

The pH measurements also showed that the freshly deionized water had an average pH value of 6.89±0.03 before being used in the experiments (Table 3). Since the experiments were conducted in the laboratory room air, the gradual dissolution of atmospheric $CO_2$ into the deionized water during a 10-hour experiment period resulted in water pH change from 6.89±0.03 to 5.68±0.06, which was observed in the control experiment with the same "cathode water Al-Tf-Al water anode" setup except without turning on the electrolysis voltage (0 V). Therefore, this bulk water pH change had little to do with the 200V-driven water electrolysis process. The same magnitude of bulk water pH change before and after the experiment was observed for the deionized water in both the anode and cathode chambers, which also supports the understanding that this bulk water pH change from the beginning to the end of the experiment was due to the gradual dissolution of atmospheric $CO_2$ into the deionized water during the 10-hour experiment period. There was no difference between the bulk-phase pH of anode chamber water (pH 5.76±0.09) and that of the cathode chamber water (5.78±0.14) at the end of the experiment. This result also points to the same underline understanding that the excess protons do not behave like typical solute molecules. Excess protons do not stay in the water bulk phase; they localize at the water-membrane interface at the $P_I$ site so that they cannot be detected by the bulk-phase pH measurement.

A further set of experiments with the setup of "cathode water Tf-Al-Tf water anode" was also conducted in triplicate. In this set of experiments, we chose to use the Tf-Al-Tf membrane system instead of the Al-Tf-Al membrane system. Since the Teflon membrane is chemically inert to protons, the use of the Tf-Al-Tf membrane system eliminated the consumption of excess protons by the aluminum corrosion process at the $P_I$ site that was demonstrated above. In this set of the experiments, no bulk-phase pH difference (ΔpH) between the anode and cathode water bodies was observed as well. As shown in Table 3, after run for 10 hours at 200V with the "cathode water Tf-Al-Tf water anode" system, the measured pH value in the anode bulk water phase (5.76±0.03) was essentially the same as that of the cathode bulk water phase (5.81±0.04). This experimental observation again indicated that the excess protons do not stay in the bulk water phase and thus cannot be measured by the bulk liquid phase pH measurement. Since liquid water is an effective proton conductor as discussed above, the excess protons produced in the anode water compartment electrostatically localize to the water-membrane interface at the $P_I$ site, where they also attract the excess hydroxyl anions of the cathode water body at the other side of the Tf-Al-Tf membrane, forming an "excess hydroxyl anions Tf-Al-Tf excess protons" capacitor-like structure as illustrated in FIG. 1.

TABLE 3

Averaged pH values measured in bulk water phase before and after 10 hours experiment with cathode water membrane water anode systems.

| Experiments | | pH of Cathode Water | pH of Anode Water |
| --- | --- | --- | --- |
| With (Al-Tf-Al) | Before | 6.89 ± 0.03 | 6.89 ± 0.03 |
| 200 V | After | 5.78 ± 0.14 | 5.76 ± 0.09 |
| With (Tf-Al-Tf) | Before | 6.71 ± 0.10 | 6.71 ± 0.10 |
| 200 V | After | 5.81 ± 0.04 | 5.76 ± 0.03 |
| With (Al-Tf-Al) | Before | 6.89 ± 0.03 | 6.89 ± 0.03 |
| control (0 V) | After | 5.68 ± 0.06 | 5.78 ± 0.02 |
| With (Tf-Al-Tf) | Before | 6.71 ± 0.10 | 6.71 ± 0.10 |
| control (0 V) | After | 5.76 ± 0.02 | 5.78 ± 0.04 |

Example 3

Figure 7:
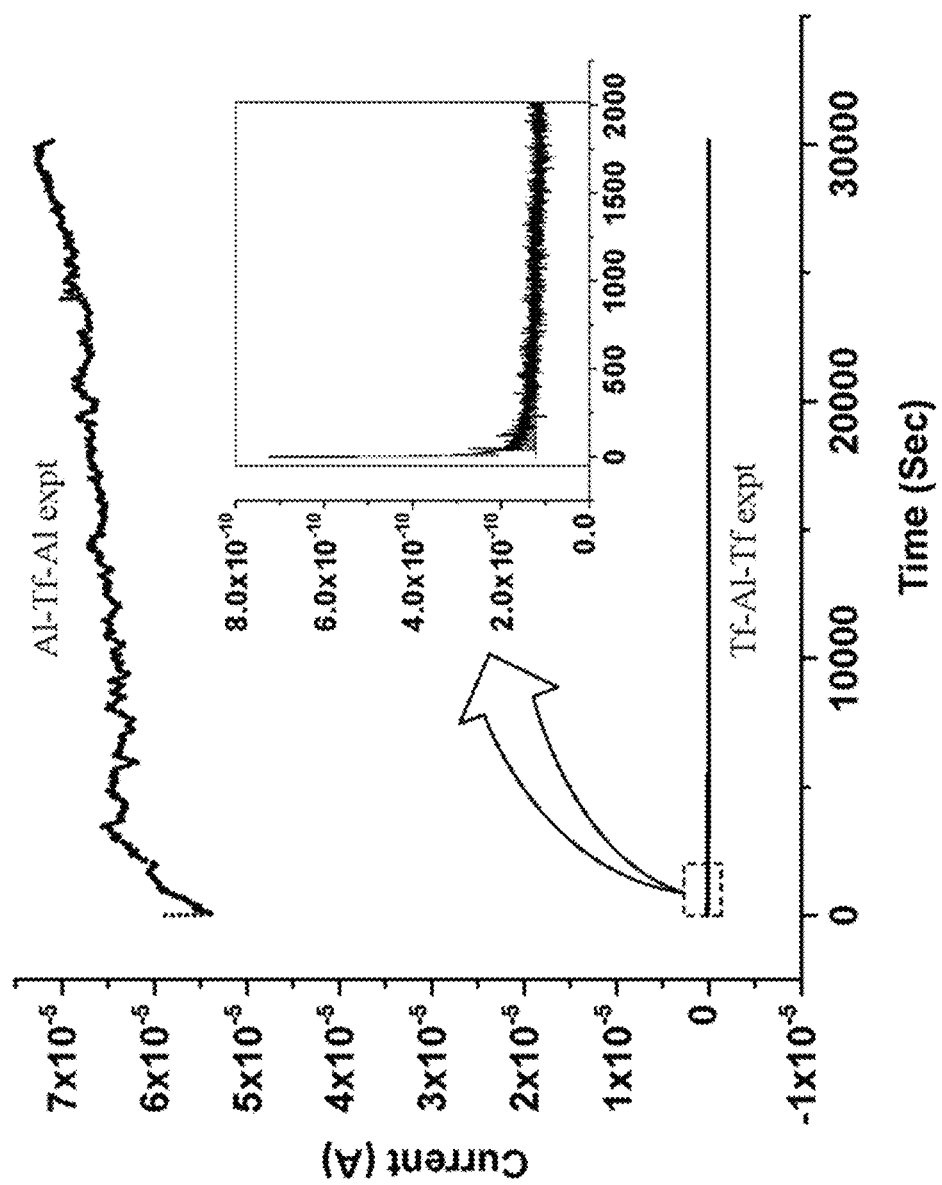
FIG. 7 presents the electric current of water electrolysis measured as a function of time with 200 V during 10 hours experimental run. The black curve shows average of three experiments with "cathode water Al-Tf-Al water anode". The blue line shows average of three experiments with "cathode water Tf-Al-Tf water anode"; and its initial part within the first 2000 seconds is plotted in an expanded scale showing the integration for the area under the curve (Inset).

Production of Excess Protons Assessed with Water Electrolysis Electric Current Measurements The proton-charging-up process in this "excess hydroxyl anions Tf-Al-Tf excess protons" capacitor system was monitored by measuring the electric current of the 200V-driven water electrolysis process as a function of time during the entire 10-hour experimental run. The data in the inset of FIG. 7 showed that the electric current of the water electrolysis process decreased with time as expected. That is, when the excess protons were generated in the anode water compartment (while the excess hydroxyl anions were generated in the cathode water compartment), this "excess hydroxyl anions Tf-Al-Tf excess protons" capacitor is being charged up by localization of the excess protons at the $P_I$ site and the excess hydroxyl anions at $N_I$ site (FIG. 7). According to the analysis, this process reached thermodynamic equilibrium after 1500 seconds (shown in the inset of FIG. 7) under this experimental condition where the curve of the water electrolysis current quickly became flat indicating the completion of the water electrolysis-coupled proton-charging-up process.

By calculating the area under the water-electrolysis current curve above the flat baseline as shown in the inset of FIG. 7, the amount of excess protons loaded onto the "excess hydroxyl anions Tf-Al-Tf excess protons" capacitor was estimated to be about $2.98 \times 10^{-13}$ moles (Table 4). The area of the Teflon membrane surface exposed to the anode water at the $P_I$ site was measured to be 2.55 cm². If that amount of excess protons were loaded at the $P_I$ site onto the Teflon membrane surface exposed to the anode water, the maximal localized excess proton density per unit area was estimated to be 1.19 nanomoles H⁺/m². Although the exact thickness of the localized excess proton layer at the $P_I$ site is yet to be determined, studies indicated that the effective thickness for this type of the electrostatically localized excess proton layer may be about 1±0.5 nm. If that is the case, then the localized excess proton density of 1.19 nanomoles H⁺/m² would translate to a localized excess proton concentration of 1.19 mM H⁺ (equivalent to a localized pH value of 2.92) at the $P_I$ site, which can explain why they can be detected by the proton-sensing Al film there.

The water electrolysis current in the "cathode water Al-Tf-Al water anode" experiment was also monitored. As shown in FIG. 7, after 5000 seconds, the water electrolysis electric current at the steady state of this experiment reached around $6.5 \times 10^{-5}$ A, which was much bigger than that (below $1 \times 10^{-10}$ A) of the "cathode water Tf-Al-Tf water anode" experiment. This large water electrolysis electric current can be attributed to the consumption of excess protons by the proton-sensing Al film at the $P_I$ site. As the proton-sensing film at the $P_I$ site consumes the excess protons, more excess protons can then be produced at the anode electrode, resulting in a significant water-electrolysis electric current. The high concentration of the electrostatically localized excess protons at the $P_I$ site thermodynamically drives the aluminum corrosion reaction in which aluminum atoms are oxidized by protons resulting in evolution of molecular hydrogen gas. During the experiment, we indeed noticed the formation of gas bubbles on the aluminum membrane surface at the $P_I$ site (FIG. 8a), which is consistent with the understanding of the localized excess protons-driven aluminum corrosion process [Eq. 5] mentioned above.

By calculating the area under the water-electrolysis current curve from the "cathode water Al-Tf-Al water anode" experiment and subtracting that of the "cathode water Tf-Al-Tf water anode" experiment, the amount of excess protons that were generated by the anode and consumed by the proton-sensing film at the $P_I$ site was able to be calculated. As shown in Table 4, during the 10-hr "cathode water Al-Tf-Al water anode" experiment, a total of $2.11 \times 10^{-5}$ moles of excess protons were generated by the anode platinum electrode. These excess protons were apparently translocated to the proton sensing film surface at the $P_I$ site and consumed there by the corrosion reaction which gives the dark brownish grey on the exposed part of the proton sensing film as shown in FIGS. 6 ($P_I$) and 8a. The amount of protons consumed per unit area was calculated to be $8.29 \times 10^{-6}$ moles per cm².

TABLE 4

Calculation of localized proton density per unit area in the "cathode water Tf-Al-Tf water anode" experiment.

| | Area under the current vs. time curve (Coulombs) | Moles of excess protons H⁺ (mol) | Localized proton density per unit area (mole H⁺/m²) | pH at $P_I$ of the Tf-Al-Tf |
|---|---|---|---|---|
| Trial 1 | $3.03 \times 10^{-8}$ | $3.14 \times 10^{-13}$ | $1.25 \times 10^{-9}$ | 2.90 |
| Trial 2 | $2.25 \times 10^{-8}$ | $2.33 \times 10^{-13}$ | $9.33 \times 10^{-10}$ | 3.03 |
| Trial 3 | $3.35 \times 10^{-8}$ | $3.47 \times 10^{-13}$ | $1.38 \times 10^{-9}$ | 2.85 |
| Average | $2.88 \times 10^{-8}$ | $2.98 \times 10^{-13}$ | $1.19 \times 10^{-9}$ | 2.92 ± 0.09 |

Example 4

Experimental Demonstration with the Three-Chamber System

Recently, in the Lee laboratory at Old Dominion University (ODU), excess protons and excess hydroxyl anions were generated utilizing a three-chamber system (comprising a cathode chamber, a Teflon sample (induction) chamber, and an anode chamber) through application of a special "open-circuit" water-electrolysis process, which is similar to the 200 system (FIG. 2). A Teflon sample chamber was sealed at both ends by two pieces of proton-sensing films placed along with an impermeable (Teflon) membrane in between. This Teflon chamber was filled with liquid water, and was then tightly fit through a specific hole in the wall that separates the anode and cathode chambers so that one of the sample chamber ends is in contact with cathode bulk liquid while the other end in contact with anode bulk liquid.

Based on the experimental observations, when excess protons were generated in the anode water body while excess hydroxyl anions were generated in the cathode chamber water through the "open-circuit" water-electrolysis process that was carried out for 20 hours, the excess protons in the anode water were localized at the water-membrane interface along the Teflon membrane surface forming a positive (P) side. The localized protons of the P side attracted the hydroxyl anions of the sample chamber water to the water-membrane interface at the other side of the Teflon membrane, forming an induced negatively charged hydroxyl anions layer (N') also shown at the INI site 212 in FIG. 2. In addition, the excess hydroxyl anions in the cathode water at the left end were localized at the water-membrane interface along the Teflon membrane surface forming a negative (N) side also shown as the excess anions layer at NI site 208 in FIG. 2. The localized hydroxyl anions of the N side attract the protons of the sample (induction) chamber water to the Teflon membrane's P' side (induced protons layer at IPI site 211 in FIG. 2) facing the induction chamber water.

Figure 9:
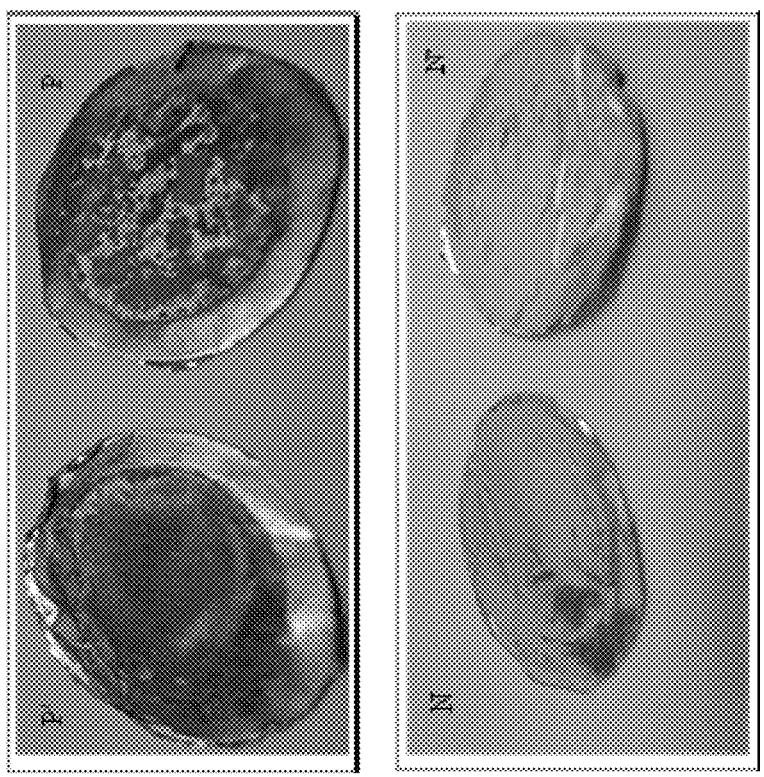
FIG. 9 presents the experimental evidence in detection of protons with proton-sensing films at the P', P, N and N' sites in the cathode water-Teflon chamber water-anode water system.

The experimental result that supports this understanding is shown in FIG. 9. The proton-sensing film placed at the P or P' side of Teflon membrane detected the localized proton activity so that its color became dark brownish grey (FIG. 9, top row); while the proton-sensing film placed at the N or N' side of Teflon membrane detected no significant proton activity so that its color remains unchanged (bottom row of FIG. 9).

Figure 10:
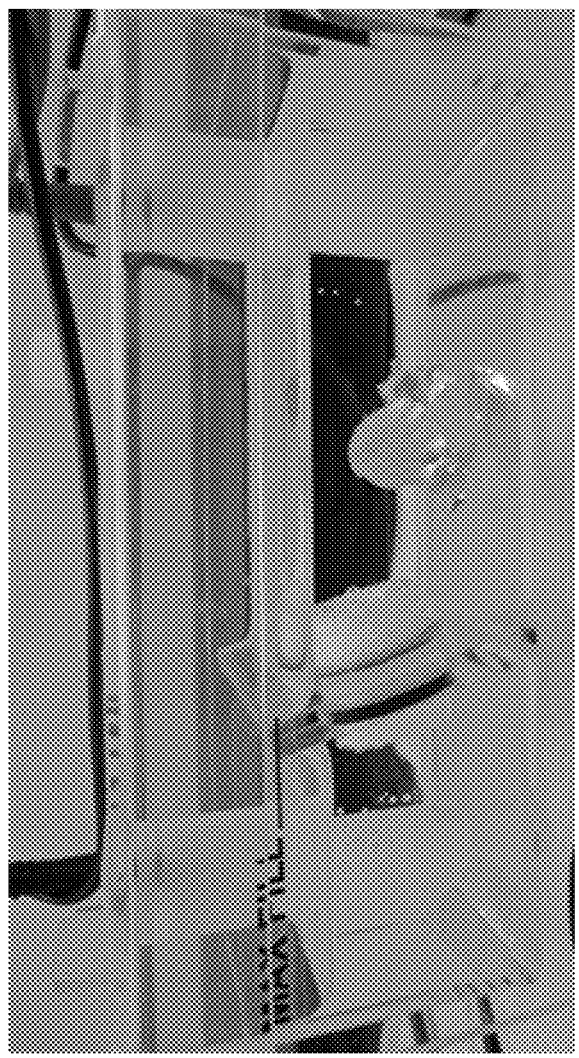
FIG. 10 presents a photograph of the cathode water-Teflon chamber water-anode water system with a piece of proton-sensing film material inserted into the anode chamber water body (at the right side).

To see if the excess protons in the anode water could stay inside the anode water body, a piece of proton-sensing film material was inserted into the anode chamber water body as shown in FIG. 10. The proton-sensing film material inserted into the anode chamber water detected no significant proton activity (the film color remained the same) during the entire 20 hour experiment (FIG. 10); whereas the localized protons were detected by the color change of the proton-sensing film placed at the P side surface at the right end of the Teflon sample (induction) chamber facing the anode water. These experimental results indicated: (i) The excess protons generated in the anode water did not stay inside the anode water body; and (ii) The localization pattern of the excess protons and hydroxyl anions along the two sides of the Teflon membrane is similar to that illustrated in FIGS. 1 and 2.

Figure 11:
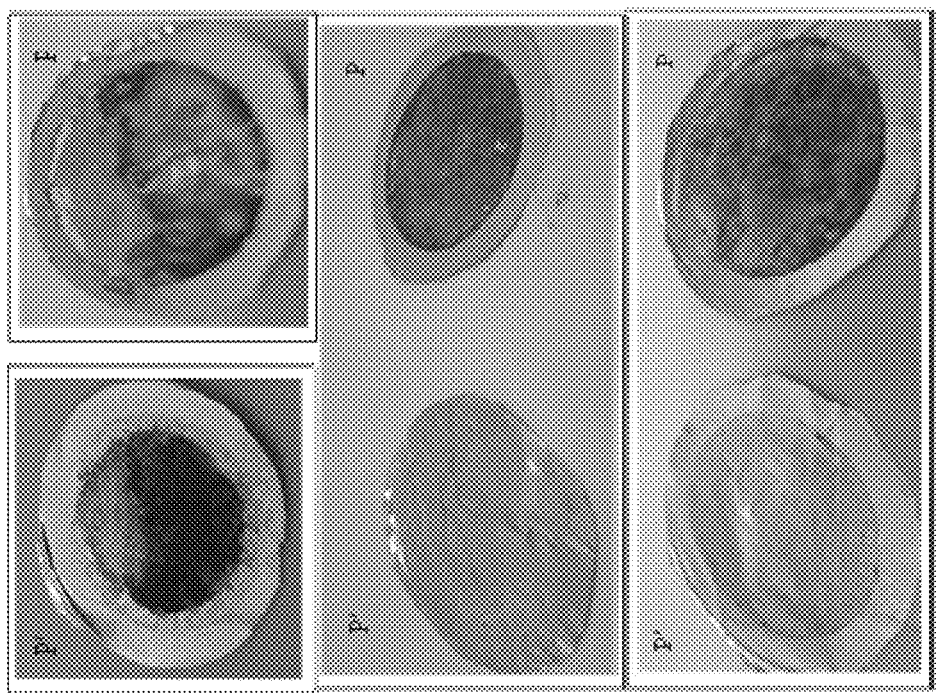
FIG. 11 presents the experimental evidence in detection of electrostatically localized protons with proton-sensing films at the P and P' sides in a cathode water-Teflon induction chamber sodium bicarbonate solution-anode water system with the presence of 10 mM (top row), 100 mM (middle row), and 400 mM (bottom row) of sodium bicarbonate water solution in the Teflon sample chamber.

A further experiment was performed by introducing certain salt (sodium bicarbonate) into the Teflon sample chamber (FIG. 10) to test the effect of sodium cations of the salt solution on the localized protons at the induced P' side in the sample chamber, in comparison with the unperturbed P side facing the anode water. The experimental results (FIG. 11) showed that the addition of 10 mM sodium bicarbonate had no significant effect on the localized protons at the P' side facing the sodium bicarbonate solution. The use of 100 mM sodium bicarbonate (in the sample chamber) led to the reduction of localized protons at the P' side by about 50%, which was monitored by the color change of the proton-sensing film at the P' side, in comparison with that of the proton-sensing film placed at the P side. It required the use of 400 mM or higher concentration of sodium bicarbonate solution in Teflon sample (induction) chamber to remove the localized protons at the P' side to a level that could not be detected by the proton-sensing film (FIG. 11, bottom row).

Based on this experimental observation, the exchange equilibrium constant of sodium ($Na^+$) cations with the localized protons was estimated to be less than $10^{-7}$. That is, the electrostatically localized protons at the water-surface interface is quite stable, in that it would require more than $10^{+7}$ times more $Na^+$ cations than the protons in the liquid phase to delocalize the protons from the water-membrane interface at the P' site. This gives confidence that the proton-electrostatic localization hypothesis is a correct and robust concept, which is employed in the present invention.

Example 5

Application of Localized Excess Protons for Utilizing Latent Heat Energy to Generate "Bonus" Proton Motive Force In this example, 1.5 V of electrolytic voltage is applied across the anode and the cathode in a multi-chamber system similar to the one illustrated in FIG. 4 that produces excess protons and hydroxyl anions forming multiple "excess protons-membrane-hydroxyl anions" capacitor-like structures for extraction of latent heat to generate additional protonic motive force (equivalent to useful Gibbs free energy) to do work such as driving ATP synthesis. In this multi-chamber system, there are 15 membranes that separate 16 liquid chambers. Each chamber contains the pH 7.0 liquid media as listed in Table 2. At the equilibrium with the excess-proton-producing water electrolysis process driven by the 1.5 V across the anode and the cathode, the membrane potential across each of the 15 membranes is 100 mV, which, if based on the delocalized proton view of Peter Mitchell's Chemiosmotic Theory, would translate to a classic pmf of only 100 mV that would not be sufficient to drive ATP synthesis to support cell growth. On the other hand, according to the data of Table 2 of the present invention, with a membrane potential of 100 mV and liquid media pH 7.0, each membrane has a total pmf of 398 mV (298 mV of it is from the local pmf) that is sufficient to drive proton users such as ATP synthase for synthesis of ATP from ADP and Pi. The total pmf of the 15 membranes is 5.97 V, of which 4.47 V is from the local pmf that is extracted from the latent heat with the localized protons at the membrane surfaces and the remainder 1.5 V is the total membrane potential. That is, the use of a 1.5 V water electrolysis process through this special system generates a total pmf of 5.97 V. In this example, 74.9% of the total pmf (5.97 V) is generated from the latent heat (thermal motion energy) by the activity of localized protons in accordance with one of the various embodiments of the present invention.

Example 6

Application of Localized Excess Protons for Utilizing Latent Heat Energy to Generate More "Bonus" Proton Motive Force In this example, 1.5 V of electrolytic voltage is applied across the anode and the cathode in a multi-chamber system similar to the one illustrated in FIG. 4 that produces excess protons and hydroxyl anions forming multiple "excess protons-membrane-hydroxyl anions" capacitor-like structures for extraction of latent heat to generate additional protonic motive force (equivalent to Gibbs free energy) to do useful work such as driving ATP synthesis. In this multi-chamber system, there are 30 membranes that separate 31 liquid chambers: each chamber contains the pH 7.0 liquid media as listed in Table 2. At the equilibrium with the excess-proton-producing water electrolysis process driven by the 1.5 V across the anode and the cathode, the membrane potential across each of the 30 membranes is 50 mV, which, if based on Mitchell's delocalized proton view, would translate to a classic pmf of only 50 mV that would not be sufficient to drive ATP synthesis to support cell growth. On the other hand, according to the data of Table 2 of the present invention, with a membrane potential of 50 mV and liquid media pH 7.0, each membrane has a total pmf of 330 mV (280 mV of it is from the local pmf) that is sufficient to drive proton users such as ATP synthase for synthesis of ATP from ADP and Pi. The total pmf of the 30 membranes is 9.9 V, of which 8.4 V is from the local pmf that is extracted from the latent heat energy with localized protons at the membrane surfaces, and the remainder 1.5 V is the total membrane potential. That is, a 1.5 V input through this special system generates a total pmf of 9.9 V. In this case, 84.8% of the total pmf (9.9 V) is generated from latent heat (thermal motion energy) by the activity of localized protons. Note, the total pmf (9.9 V) generated in this example is significantly higher than that in Example 5 that uses 15 membranes (each with 100 mV of membrane potential). This result demonstrates that the use of more (30) membranes (each with 50 mV of membrane potential) can indeed generate more local pmf (8.4 V) from latent heat than that (4.47 V) of Example 5 using 15 membranes (each with 100 mV of membrane potential) even though the same 1.5 V of electrolytic voltage is used in both Examples 5 and 6, which is consistent with the predicted feature from the present invention.

Example 7

Application of Localized Excess Protons for Utilizing Latent Heat Energy to Generate Much More "Bonus" Proton Motive Force In this example, 1.5 V of electrolytic voltage is applied across the anode and the cathode in a multi-chamber system similar to the one illustrated in FIG. 4. In this multi-chamber system, there are 60 membranes that separate 61 liquid chambers: each chamber contains the pH 7.0 liquid media as listed in Table 2. At the equilibrium with the excess-proton-producing water electrolysis process driven by the 1.5 V across the anode and the cathode, the membrane potential across each of the 60 membranes is 25 mV, which, if based on Mitchell's delocalized proton view, would translate to a classic pmf of only 25 mV that would not be sufficient to drive ATP synthesis to support cell growth. On the other hand, according to the data of Table 2 of the present invention, with a membrane potential of 25 mV and liquid media pH 7.0, each membrane has a total pmf of 288 mV (263 mV of it is from the local pmf) that is sufficient to drive proton users such as ATP synthase for synthesis of ATP from ADP and Pi. The total pmf of the 60 membranes is 17.28 V, of which 15.78 V is from the local pmf that is extracted from latent heat energy with localized protons and the remainder 1.5 V is the total membrane potential. That is, the use of a 1.5 V water electrolysis energy input generates a total pmf of 17.28 V. In this case, 91.3% of the total pmf (17.28 V) is generated from latent heat (thermal molecular motion energy) extracted by the activity of localized protons. Note, this total pmf (17.28 V) is much higher than that in Example 6 that uses 30 membranes (each with 50 mV of membrane potential). This again demonstrates that the application of more membranes (60, each with 25 mV of membrane potential here) in accordance with one of the various embodiments of the present invention can indeed extract much more latent heat energy by localized protons to generate much more local pmf (15.78 V) than that of Examples 5 and 6 with the same 1.5 V electrolysis voltage input.

Example 8

Application of Localized Excess Protons for Utilizing Latent Heat Energy to Generate Additional Proton Motive Force—Biological Implications Table 5 shows pmf values calculated from Eqs. 6-8 based on the well-established experimental data of *Bacillus pseuodofirmus* OF4 (alkalophilic bacteria) under its culture medium pH, cytoplasmic pH, and transmembrane potential conditions. The calculated pmf as a function of the culture medium pH is displayed in FIG. 12, in comparison to the "classic" pmf contribution. From these calculated results, it is apparent that the surface localized protons control the overall strength of the proton motive force.

Figure 12:
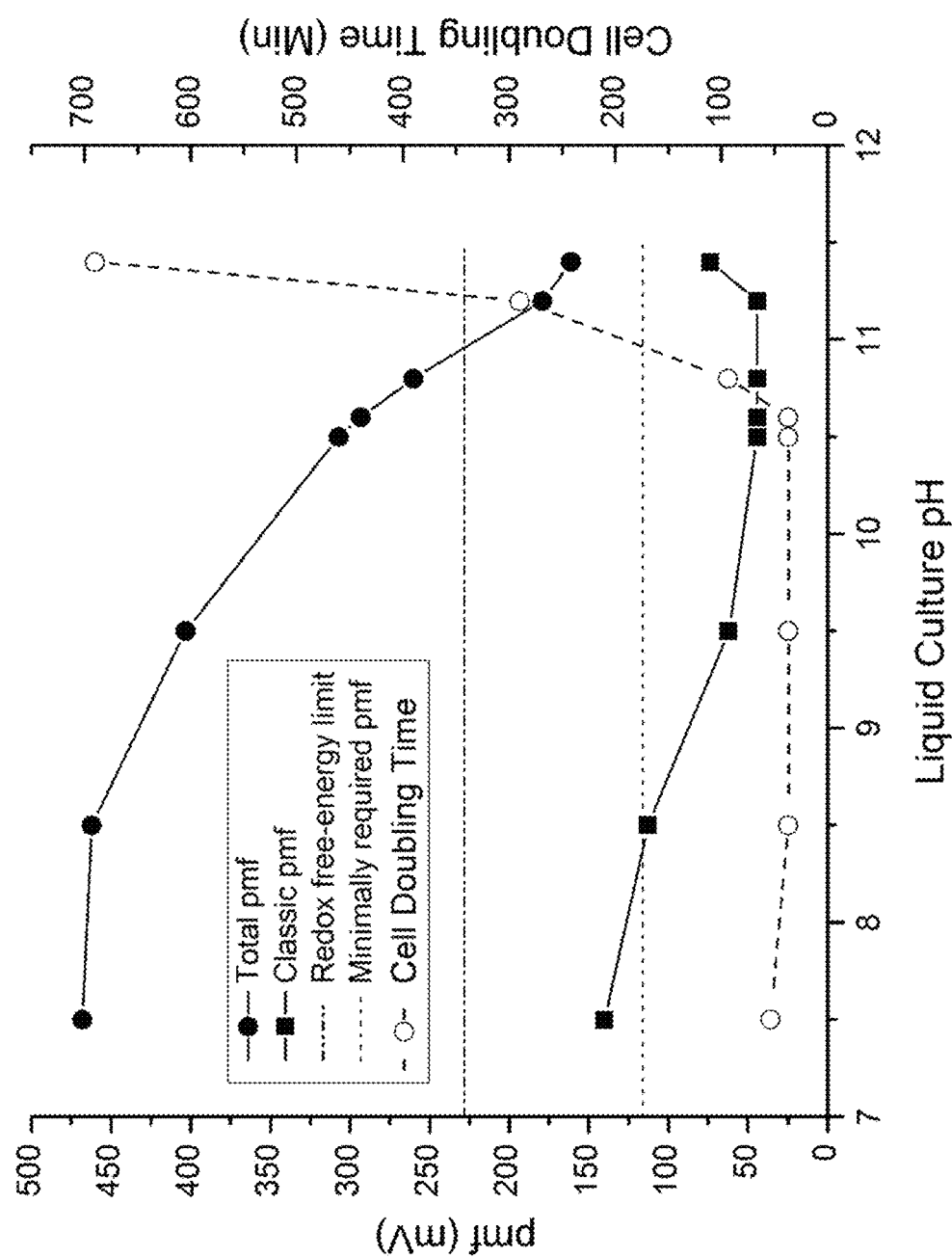
FIG. 12 presents the calculated total and classic pmf values of *Bacillus pseuodofirmus* OF4 as a function of external pH compared to the minimum value required to synthesize ATP and to the maximum value allowed by the Second Law of Thermodynamics.

As shown in FIG. 12, the total pmf values including the pmf contribution from the localized protons are well above the minimally required value of at least 116 mV, while the classical pmf is significantly below this minimum requirement for at all culture pH values above 8.5. The minimum pmf value is what is needed to overcome the known phosphorylation potential (−497 mV) for ATP synthesis through the ATP synthase with a proton-to-ATP ratio of 13/3 (497 mV/4.33=116 mV). The proton-to-ATP ratio of 13/3 used in this calculation for the minimally required value of 116 mV is consistent with the known structure of *Bacillus pseuodofirmus* $F_0F_1$-ATP synthase, which has 3 catalytic sites for ATP synthesis driven by a flow of 13 protons per revolution through the 13 c-subunits in its nanometer-scale molecular turbine ring.

The calculated total pmf values as listed in Table 5 are in a range from 468 mV to 161 mV, which are all above the minimally required value of 116 mV. Especially, when the culture medium pH in a range from 7.5 up to 10.8, the calculated total pmf value are in a range from 468 mV to 260 mV, which is well above the minimally required 116 mV. This result can explain why the *Bacillus pseuodofirmus* OF4 culture can keep such an excellent growth rate (doubling times less than 100 min) in this culture pH range from 7.5 to 10.8. Furthermore, the decrease in pmf when the liquid culture pH is raised beyond 10.8, due to decreased contribution from the localized protons, matches well with the dramatic increase in growth doubling times (decreased growth rate).

Theoretically, when the total pmf is reduced to around 116 mV, the bioenergetic system would reach equilibrium and the molecular turbine of $F_0F_1$-ATP synthase would stop running and the culture growth could completely stop. When the total pmf values is reduced to a value somewhat closer the minimally required value of 116 mV, such as 179 mV and 161 mV as calculated at the culture pH 11.2 and 11.4, the growth rate would grammatically decrease. This understanding, for the first time, provides an excellent bioenergetics explanation in correlating with the dramatic reduction of growth rate observed at culture pH 11.2 and 11.4 (Table 5 and FIG. 12).

The successful elucidation of the decades-longstanding energetic conundrum of alkalophilic bacteria *Bacillus pseuodofirmus* OF4 as to how they are able to synthesize ATP as demonstrated again in this Example 8, also indicated that the local pmf values calculated through Eqs. 3 and 6-8 using the parameters reported above are indeed about right.

TABLE 5

*Bacillus pseuodofirmus* OF4 measured properties ($pH_{pB}$, $pH_{nB}$, $\Delta\psi$) and calculated quantities using Eqs. 6-8. The cation concentrations and proton exchange equilibrium constants are from Table 1 and the temperature T = 298 K. The "local" pmf is the last term in Eq. 8 due to the localized protons, while the first two terms of Eq. 8 give the "classic" pmf.

| $pH_{pB}$ | $pH_{nB}$ | $\Delta\psi$ (mV) | $[H_L^+]^0$ (molar) | Exchange reduction factor | $[H_L^+]$ (molar) | Local pmf (mV) | Classic pmf (mV) | Total pmf (mV) |
|---|---|---|---|---|---|---|---|---|
| 7.5 | 7.5 | 140 | $1.92 \times 10^{-2}$ | 1.71 | $1.12 \times 10^{-2}$ | 328 | 140 | 468 |
| 8.5 | 7.7 | 160 | $2.19 \times 10^{-2}$ | 8.60 | $2.54 \times 10^{-3}$ | 349 | 113 | 462 |
| 9.5 | 7.5 | 180 | $2.46 \times 10^{-2}$ | 133 | $1.85 \times 10^{-4}$ | 341 | 62 | 403 |

TABLE 5-continued

Bacillus pseuodofirmus OF4 measured properties ($pH_{pB}$, $pH_{nB}$, $\Delta\psi$) and calculated quantities using Eqs. 6-8. The cation concentrations and proton exchange equilibrium constants are from Table 1 and the temperature T = 298 K. The "local" pmf is the last term in Eq. 8 due to the localized protons, while the first two terms of Eq. 8 give the "classic" pmf.

| $pH_{pB}$ | $pH_{nB}$ | $\Delta\psi$ (mV) | $[H_L^+]^0$ (molar) | Exchange reduction factor | $[H_L^+]$ (molar) | Local pmf (mV) | Classic pmf (mV) | Total pmf (mV) |
|---|---|---|---|---|---|---|---|---|
| 10.5 | 8.2 | 180 | $2.46 \times 10^{-2}$ | $2.77 \times 10^4$ | $8.88 \times 10^{-7}$ | 263 | 44 | 307 |
| 10.6 | 8.3 | 180 | $2.46 \times 10^{-2}$ | $6.06 \times 10^4$ | $4.06 \times 10^{-7}$ | 249 | 44 | 293 |
| 10.8 | 8.5 | 180 | $2.46 \times 10^{-2}$ | $3.39 \times 10^5$ | $7.27 \times 10^{-8}$ | 216 | 44 | 260 |
| 11.2 | 8.9 | 180 | $2.46 \times 10^{-2}$ | $2.01 \times 10^7$ | $1.23 \times 10^{-9}$ | 135 | 44 | 179 |
| 11.4 | 9.6 | 180 | $2.46 \times 10^{-2}$ | $2.13 \times 10^8$ | $1.16 \times 10^{-10}$ | 87 | 74 | 161 |

Example 9

Application of Localized Excess Protons for Utilizing Latent Heat to Generate Additional Proton Motive Force Revealing a Special Biological Energy Function As noted, the pmf values predicted by Eq. 8 for *Bacillus pseuodofirmus* OF4 were all larger than the minimum value required for ATP synthesis; however, the pmf values for the culture at pH 7.5, 8.5, 9.5, and 10.5 of 468 mV, 462 mV, 403 mV, and 307 mV, respectively, are all significantly larger than the maximum value of 228 mV that would be allowed by the First and the Second Laws of Thermodynamics (see FIG. 12). Since the additional "bonus" pmf is somehow from a special utilization of latent heat energy, it perfectly obeys the First Law (Conservation of Energy and Mass). The implication of the "bonus" local pmf values listed in Table 5 (and Table 2) is on the Second Law of Thermodynamics, which states the impossibility of utilizing or extracting the dissipated latent heat energy from ambient temperature environment to do useful work.

The maximum pmf value allowed by the conventional Thermodynamics for the entire oxidative-respiratory phosphorylation system such as the one in *Bacillus pseuodofirmus* OF4 is only 228 mV as presented in FIG. 12 as a redox Gibbs free energy limit. This number can be calculated from the redox potential difference between the electron donor NADH to the terminal electron acceptor $O_2$ in this system which is known to be about 1140 mV (Nicholls and Ferguson 2013 Bioenergetics, 27-51, Academic Press) and from the number of protons that are translocated across the membrane for each pair of electrons from NADH to pass through the respiratory chain to $O_2$, it drives the translocation of 10 protons across the membrane from the cytoplasm to the culture medium outside the cell. That is, it couples the translocation of 5 protons per electron across the membrane. Therefore, the thermodynamically predicted maximum pmf that could be generated is about 228 mV per proton (1140 mV/5 protons) under the standard conditions (pH 7.0).

The classic Mitchellian pmf values calculated from the first two terms of Eq. 8 as listed in Table 5 and presented in FIG. 12 are far below this 228 mV limit. When the bacteria culture medium pH was around 10.5, the classic Mitchellian pmf value got as low as 44 mV which clearly could not explain the observed excellent cell growth rate. Apparently, it is the local pmf which can now be calculated through the third term of Eq. 8 from the localized proton concentration at the water-membrane interface that contributes more than 200 mV of "bonus" pmf in supporting the observed excellent cell growth rate. At culture medium pH 10.5, the local pmf is 263 mV which represents as much as 85% of the total pmf (307 mV) while the classic Mitchellian pmf (44 mV) represents only 15% of the true total pmf.

The total pmf (307 mV) is significantly higher than the conventionally predicted pmf upper limit of 228 mV for the oxidative-respiratory phosphorylation system, which is also known as the thermodynamics limit. Therefore, if the observed pmf value in the oxidative-respiratory phosphorylation system such as the one in *Bacillus pseuodofirmus* OF4 is truly exceeds this limit, it could indicate that something special in the biological system might not necessarily have to obey the Second Law.

Example 10

Application of Localized Excess Protons for Extraction of Latent Heat Energy Revealing a Special Anti-Second-Law Energy Function Regarding whether a total pmf value much higher than the thermodynamics limit of 228 mV would imply that electrostatically localized protons do not exist at the cell membrane surface, or that they are not taken into account properly by Eqs. 6-8, it is now believed that the work done by the localized protons in producing ATP is not constrained by the Second Law of Thermodynamics for the following reasons.

First, the localized protons are not entirely free to move; they are electrostatically held at the membrane surface. Consequently, their thermal (Brownian) motion will cause some to enter the opening of the ATP synthase and be used to produce ATP. Secondly, the localized protons must not be directly coupled to the redox proton pumps. If they were, they would be constrained by the Second Law and they would also disrupt the respiratory process. A natural explanation of why this does not occur is that the exit points for the translocated protons must be outside of the surface layer of the electrostatically localized protons. Furthermore, to effectively make use of the localized proton thermal motion, the proton entry point for ATP synthase must be inside the localized proton surface layer. In this scenario, the redox proton pump activity interacts with the proton activity in the bulk liquid phases but not with that of the localized proton layer at the liquid-membrane interface. Only the transmembrane electric potential difference and the bulk-phase proton activity at the two sides of the membrane interact and equilibrate with the proton-pumping respiratory chain activity which is driven by 228 mV per proton and follows the Second Law. The localized proton thermal motion provides additional free energy that may be utilized by the ATP synthase.

Regarding the determination of the structures of the redox complexes in sufficient detail to confirm, or disprove, these conjectures, the structures of bacterial respiratory membrane protein complexes are not well known yet. However, they are believed to be very similar to those in mitochondria, which have been more extensively studied. Indeed, the known structures of the mitochondrial respiratory protein complexes, as determined by electron microscopy and other molecular structural studies (Dudkina et al., 2010 Biochimica Et Biophysica Acta-Bioenergetics, 1797(6-7): 664-670), fit well with the fundamental understanding and principle associated with the present invention. Every one of the mitochondrial respiratory protein pumping complexes I, III and IV are indeed protruded away from the membrane surface by about 1-3 nm into the bulk liquid, while the end (proton mouth) of the ATP synthase (complex V) is located indeed rightly at the membrane surface within the localized proton layer as predicted by the present invention.

Therefore, the electrostatically localized protons in combination with asymmetric structural features of the biological membrane especially in regard to positions of the proton pump outlets and the mouth of the localized proton users such as that of the ATP synthase (complex V) with respect to the localized proton layer along the p-side of the membrane may constitute this special function, which is not necessarily constrained by the Second Law of Thermodynamics. It is the electrostatic proton localization with the effect of water as a proton conductor that enables the formation of localized excess proton layer at water-membrane interface over the mouths of the pmf users including the $F_0F_1$-ATP synthase. The formation of a localized excess proton layer at water-membrane interface apparently result in some kind of "negative entropy effect" that bring the excess protons to the mouths of the pmf users where the protons can utilize their molecular thermal motions (latent heat energy) possibly including their Brownian motion to push through the doors of $F_0F_1$-ATP synthase in driving ATP synthesis.

In order to avoid the situation of localized excess protons pushing the "wrong doors" such as the exit sites of the respiratory electron-transport-coupled proton pumps, the billion-year natural evolution process apparently has already solved this potential problem by protruding all the proton pump exits of the respiratory protein complexes I, III and IV a few nanometers away from the membrane surface into the bulk liquid phase while keeping the mouth of the ATP synthase (complex V) right at the membrane surface for the best benefit of utilizing the localized excess protons there. In this way, the localized excess protons at the water-membrane interface along the membrane surface can perfectly go through the mouth of ATP synthase (complex V) and they will not be able to touch the "doors" of the proton-pumping respiratory protein complexes I, III and IV that are protruded into the bulk liquid phase well out of the localized excess layer as we can now start to understand.

The benefit for such an apparently Anti-Second-Law biological function is significant. The application of Eq. 9 has now, for the first time, been able to calculate the "local pmf" as listed in Table 5, which represents the amount of pmf (equivalent to Gibbs free energy) extracted by this Anti-Second-Law biological function from the dissipated ambient-temperature heat energy of the bacteria culture medium environment. The pmf (useful free energy) extracted from the latent heat energy may represent as much as 85% of the total pmf (307 mV) for the *Bacillus pseuodofirmus* growing at pH 10.5, which beautifully explains the observed excellent cell growth rate that Peter Mitchell's chemiosmotic theory completely fails to explain.

From this example, it is now also clear that the creation of localized excess protons contributes to conferring this special Anti-Second-Law energy technology function that enables the utilization of dissipated latent heat from the ambient temperature environment to generate additional proton motive force (equivalent to Gibbs free energy) that can be employed to do useful work. Furthermore, the asymmetric features of the membrane, especially with regarding to the geometric position of proton producers with their outlets extended well into the bulk phase liquid while the mouths of proton users being rightly within the localized excess protons layer along the membrane surface, is also beneficial to effectively employing the localized excess protons to serve as the key part of the special Anti-Second-Law energy technology function. This conclusion is also consistent with the fundamental understanding and the sprit demonstrated through the present invention. For example, as mentioned above, it is a preferred practice to place the proton-generating anode electrode well into the bulk phase liquid as illustrated in FIGS. 1-4 to produce more desirable results in accordance of the present invention with various embodiments.

While the present invention has been illustrated by description of several embodiments and while the illustrative embodiments have been described in considerable detail, it is not the intention of the applicant to restrict or in any way limit the scope of the invention claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of applicant's general inventive concept.

What is claimed is:

1. A method for creating localized excess protons concentrations with an excess proton production and utilization system comprising using an open-circuit water electrolysis process with a pair of anode and cathode electrodes in a liquid membrane chamber system forming and using excess protons associated with an excess protons-membrane-anions capacitor system to enable a series of energy recycle process functions with utilization of latent heat energy for at least one of:
   a) utilization of latent heat molecular thermal motion energy for energy recycling and renewing of fully dissipated waste heat energy in ambient temperature environment to generate local proton motive force equivalent to Gibbs free energy to do useful work;
   b) treatment comprising protonation and proton-etching of a substrate material by forming and utilizing excess protons associated with an excess protons-membrane-hydroxyl anions capacitor system;
   c) production and conversion of local excess protons proton motive force to another ion motive force equivalent to Gibbs free energy for a series of other cation species for utilization of latent heat molecular thermal motion energy from the group consisting of $Na^+$, $K^+$, $Li^+$, $Rb^+$, $Cs^+$, $Co^{++}$, $Ni^{++}$, $Zn^{++}$, $Cu^{++}$, $Fe^{++}$, $Mn^{++}$, $Ca^{++}$, $Mg^{++}$; and
   d) combinations thereof.

2. The method according to claim 1, wherein the special excess proton production and utilization system comprises:
   a chamber wall comprising water impermeable and chemically-inert materials that are unreactive under high power voltage, the water impermeable and chemically-inert materials comprising polytetrafluoroethylene, plastics, and glasses;
a substrate film joining with the chamber wall using a water-tight seal, resulting in two separate chambers: an anode water chamber and a cathode water chamber;
a pair of anode and cathode electrodes placed into an anodic (P) liquid bulk phase and a cathodic (N) liquid bulk phase;
and a direct current voltage source that is used across the anode and cathode electrodes to drive an open-circuit water electrolysis process for production of excess protons in the anode chamber and production of hydroxyl anions in the cathode chamber to form and use an excess protons-substrate-hydroxyl anions capacitor-like system.

3. The method according to claim 1, wherein the special excess proton production and utilization system comprises:
a chamber wall comprising water impermeable and chemically-inert materials;
two substrate films joining with the chamber wall using a water-tight seal, resulting in three separate chambers: an anode water chamber, an induction chambers, and a cathode water chamber;
a pair of anode and cathode electrodes placed into an anodic (P) liquid bulk phase and a cathodic (N) liquid bulk phase;
and a direct current voltage source that be used across the anode and cathode electrodes to drive an open-circuit water electrolysis process for production of excess protons in the anode chamber and hydroxyl anions in the cathode chamber to simultaneously form and use two excess protons-substrate-hydroxyl anions capacitor-like systems.

4. The method according to claim 1, wherein the special excess proton production and utilization system comprises:
a chamber wall comprising water impermeable and chemically-inert materials;
three substrate films joining with the chamber wall using a water-tight seal, resulting in the four separate chambers: an anode water chamber, an induction chambers, another induction chamber, and a cathode water chamber;
a pair of anode and cathode electrodes placed into an anodic (P) liquid bulk phase and a cathodic (N) liquid bulk phase;
and a direct current voltage source that is used across the anode and cathode electrodes to drive an open-circuit water electrolysis process for production of excess protons in the anode chamber and hydroxyl anions in the cathode chamber to simultaneously form and use three excess protons-substrate-hydroxyl anions capacitor-like systems.

5. The method according to claim 1, wherein the special excess proton production and utilization system comprises:
a number of induction chambers that is selected from the group consisting of 0,1, 2, 3, 4, 5, 6, 7, 8, 10, 11, 12, 13, 14, 15, 17, 18, 19, 20, 21, 22, 23, 24, 25, 26, 27, 28, 29, 30, 40, 50, 60, 70, 90, 100 and a number of induction chambers greater than 100;
a number of substrate films that is selected from the group consisting of 1, 2, 3, 4, 5, 6, 7, 8, 10, 11, 12, 13, 14, 15, 17, 18, 19, 20, 21, 22, 23, 24, 25, 26, 27, 28, 29, 30, 31, 41, 51, 61, 71, 81, 91, 101, and a number of substrate films greater than 101;
a direct current electric voltage applied across the anode and cathode electrodes, the direct current electric voltage selected from the group consisting of 1.23 V, 1.5 V,2 V,3 V,4 V,5 V, 6 V, 7 V, 8V, 10 V, 11V, 12 V, 13 V, 14 V, 15 V, 17 V, 18 V, 19 V, 20 V, 21 V, 22 V, 23 V, 24 V, 25 V, 26 V, 27 V, 28 V, 29 V, 30 V, 31 V, 32 V, 35 V, 36 V, 40 V, 50 V, 60 V, 70 V, 80 V, 90 V, 100 V, 150 V, 200 V, 250V, 300 V, 400 V, 500 V, 600 V, 700 V, 800 V, 900 V, 1000V, 1200 V, 1500 V, 2000 V, 2500 V, 3000 V, 4000V, 5000 V, 6000 V, 8000 V, 10,000 V, 12,000 V, 15,000 V, 20,000 V, 25,000V and 30,000 V;
and an effective concentration of the localized excess protons at a water-substrate interface is at a value selected from the group consisting of 0.1 mM, 1 mM, 2 mM, 3 mM, 5 mM, 10 mM, 20 mM, 30 mM, 40 mM, 50 mM, 60 mM, 70 mM, 80 mM, 90 mM 100 mM, 120 mM, 150 mM, 200 mM, 300 mM, 500 mM, 1 M, 2 M, 3 M, 5M and 10 M.

6. The method according to claim 5, wherein an effective concentration of the localized excess protons at the water-substrate interface is modulated by introducing salts including sodium bicarbonate and potassium bicarbonate into an induction chamber for cation exchange with localized protons at an IPI site.

7. The method according to claim 5, wherein an effective concentration of electrostatically localized protons at an equilibrium of cation exchange is calculated as:

$$[H_L^+] = \frac{[H_L^+]^0}{\prod_{i=1}^{n}\left\{K_{Pi}\left(\frac{[M_{pB}^{i+}]}{[H_{pB}^+]}\right)+1\right\}}$$

wherein $[H_L^+]^0$ comprises an effective concentration of localized protons without cation exchange, $K_{Pi}$ comprises an equilibrium constant for non-proton cations ($M^{i+}$) to exchange for localized protons at a water-membrane interface, $[M_{pB}^{i+}]$ comprises a concentration of non-proton cations in induction chamber liquid medium and $[H_{pB}^+]$ comprises a proton concentration in a bulk phase of the induction chamber liquid medium.

8. The method according to claim 1, wherein the substrate material to be treated is selected from the group consisting of protonatable materials including (poly)aniline and metal surfaces including aluminum, iron, copper and combinations thereof.

9. The method according to claim 1, wherein the anode and cathode electrode materials are selected from the group consisting of metallic platinum, palladium, gold, copper, stainless steel, graphite, micrometer carbon fiber materials, nanometer carbon fiber materials and combinations thereof.

10. The method according to claim 1, wherein the proton-utilization system creates a special polymer film with an asymmetric proton distribution across the film material to confer some special functions including diodic properties by protonating film material including (poly)aniline at one PI site side through the following protonation reaction:

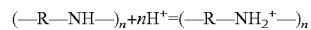

while deprotonating at the other NI site side of the film material according to the following de-protonation process reaction:

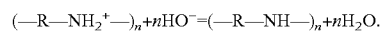

11. The method according to claim 1, wherein the proton-utilization system provides a proton-etching process used as a micrometer or nanometer fabrication tool with an acid-resistant material as a mask coating material to create proton-etching patterns on a substrate.

12. The method according to claim 1, wherein the proton-utilization system for protonation of synthetic substrate materials and proton-etching of micrometer or nanometer materials is operated in a pure water environment with neutral pH to obtain treated substrate directly as a clean product comprising a cleanness of pure water without any additional cleaning steps.

13. The method according to claim 1, wherein an effective concentration of said localized excess protons at a water-substrate interface is selected from the group consisting of 0.1 mM, 1 mM, 2 mM, 3 mM, 5 mM, 10 mM, 20 mM, 30 mM, 40 mM, 50 mM, 60 mM, 70 mM, 80 mM, 90 mM 100 mM, 120 mM, 150 mM, 200 mM, 300 mM, 500 mM, 1 M, 2 M, 3 M, 5M, 10 M and a range bounded by any two of these values.

14. The method according to claim 1, wherein the forming and using of an excess protons-substrate-hydroxyl anions capacitor-like system comprises a characteristic feature consistent with predictions from the proton electrostatic localization theory.

15. The method according to claim 1, wherein the forming and using excess protons associated with an excess protons-membrane-hydroxyl anions capacitor-like system does not require any conventional acid chemicals including nitric and sulfuric acids.

16. The method according to claim 1, wherein the utilization of latent heat energy for generating proton motive force comprises a special energy recycling- and renewing-related technology process comprising:
   a) generating excess protons in an anode liquid chamber while creating excess hydroxyl anions in a cathode liquid chamber using an open-circuit water-electrolysis process;
   b) generating excess protons that electrostatically localize primarily along the water-membrane interface at a PI site and excess anions that electrostatically localize primarily along a water-membrane interface at a NI site;
   c) using the excess protons at the PI site in conjunction with the excess anions at the NI site to induce electrostatically the formation of the induced anions at INI site and the induced protons at IPI site in the induction liquid chambers;
   d) forming the electrostatically localized protons at the water-membrane interface to result in the formation of multiple localized protons-membrane-anions capacitor-like structures;
   e) forming multiple localized protons-membrane-anions capacitor-like structures resulting in the formation of a membrane potential across each of the membranes;
   f) creating additional local proton motive force in addition to generating membrane potential from an entropy effect of localized protons having a thermal motion energy to drive nanometer scale molecular machines such as $F_0F_1$-ATP synthase embedded in the membrane;
   g) utilizing a total proton motive force comprising a membrane potential and a local proton motive force from localized protons at a PI site and IPI sites to do work as protons flow across each of the membranes through membrane-embedded ATP synthase in driving ATP synthesis from ADP and Pi; and
   h) collecting molecular hydrogen and oxygen gas products at a cathode and anode, respectively.

17. The method according to claim 1, wherein the liquid membrane chamber system comprises a multi-chamber excess proton production and utilization system comprising:
   a) multiple membranes placed between an anode chamber and a cathode chamber, forming multiple induction chambers among multiple membranes;
   b) a chamber wall comprising water impermeable and chemically-inert materials; and
   c) proton users comprising ATP synthase embedded within each of the multiple membranes.

18. The method according to claim 1, wherein the energy recycle process functions comprise a feature that employs multiple membranes, each with a relatively smaller membrane potential, in a multi-chamber system that can be employed with use of a relatively small electrolysis voltage for generating excess protons to extract latent heat molecular thermal motion energy to create a total pmf value much larger than an input electrolysis voltage.

19. The method according to claim 1, wherein the energy recycle process functions comprise a feature where generated local proton motive force (pmf) from extraction of latent heat energy may be calculated according to:

$$\text{Local } pmf = \frac{2.3RT}{F}\log_{10}(1 + [H_L^+]/[H_{pB}^+])$$

where R is a gas constant, T is absolute temperature, F is Faraday's constant, $[H_L^+]$ is a concentration of surface localized protons, and $[H_{pB}^+]$ is a proton concentration in an anode bulk aqueous phase.

20. The method according to claim 1, wherein the energy recycle process functions place a proton-generating anode electrode well into a bulk phase liquid to keep the mouths of the proton users being located within a localized excess protons layer along a membrane surface to utilize a latent heat associated with thermal motion energy of localized protons to perform useful work including synthesis of ATP.

* * * * *